United States Patent [19]

Baile et al.

[11] Patent Number: 5,670,162
[45] Date of Patent: Sep. 23, 1997

[54] METHOD AND DEVICE FOR IMPLANTATION OF LARGE DIAMETER OBJECTS IN BOVINES

[75] Inventors: Clifton Augustus Baile, Chesterfield; Jeffrey Wilson Day, Manchester; Thomas Riley Hampton, II, St. Charles; Thomas Richard Kasser, Chesterfield; James Brian Pike, St. Peters; Jonathan Paul Smith, Pacific; Lyle Elmore Ziemann, Chesterfield, all of Mo.

[73] Assignee: Monsanto Company, St. Louis, Mo.

[21] Appl. No.: 459,921

[22] Filed: Jun. 2, 1995

Related U.S. Application Data

[62] Division of Ser. No. 270,196, Jul. 1, 1994.

[51] Int. Cl.$^6$ ........................................ A23K 1/18
[52] U.S. Cl. ...................... 424/438; 424/422; 424/423; 424/473; 604/892.1
[58] Field of Search ................... 424/438, 422, 424/423; 604/473, 892.1

[56] References Cited

U.S. PATENT DOCUMENTS

| | | | |
|---|---|---|---|
| 1,555,711 | 9/1925 | Hershinger | 222/327 |
| 1,645,950 | 9/1927 | Haas | 604/58 |
| 1,929,154 | 10/1933 | Sundock | 128/266 |
| 2,059,966 | 11/1936 | Kaufman et al. | 128/260 |
| 2,086,580 | 7/1937 | Shirley | 128/234 |

(List continued on next page.)

FOREIGN PATENT DOCUMENTS

| | | | |
|---|---|---|---|
| 0 374 120 | 6/1990 | European Pat. Off. | A61K 47/10 |
| 92/00728 | 1/1992 | WIPO | A61K 9/22 |
| 92/16194 | 10/1992 | WIPO | A61K 9/22 |
| 94/04183 | 3/1994 | WIPO | A61K 37/36 |
| 94/04187 | 3/1994 | WIPO | A61K 39/00 |

OTHER PUBLICATIONS

W. J. Enright, et al., Effects of long-term administration of pituitary-derived bovine growth hormone and estradiol on growth in steers. Abstract, J. Anim. Sci 1990 vol. 68: 2345–2356.

R. L. Preston, et al., Comparative effects of BST and steroidal growth promotants in feedlot steers. Abstract 71, J. Animal Science 67, Suppl. 1: 215, 1989.

W. M. Moseley, et al., Recombinant bovine somatotropin improves growth performance in finishing beef steers. J. Animal Science 1992 70:412–425, Abstract . . . .

R. J. Early, et al., Growth and metabolism in somatotropin-treated steers. J. Animal Science 1990 68: 4134–4143, Abstract . . . .

D. L. Hancock, et al., Titration of the recombinant bovine somatotropin dosage that maximizes the anabolic response in feedlot steers. J. Animal Science 1990 68: 4117–4121, Abstract . . . .

P. P. Groenewegen, et al., Effect of bovine somatotropin on the grwoth rate, hormone profiles and carcass composition of holstein bull calves. Domestic Animal Endocrinology, vol. 7(1): 43–54, 1990, Abstract . . . .

E. P. Stanisiewski, et al., Milk Yield, health, and Reproductoin of dairy cows given somatotropin (somavubove) beginning early postpartum. J. Dairy Science 1992 75: 2149–2164, Abstract . . . .

R. J. Early, et al., Growth and metabolism in somatotropin-treated steers: II. Carcass and noncarcass tissue components and chemical composition. J. Animal Science 1990 68: 4144–4152, Abstract . . . .

(List continued on next page.)

*Primary Examiner*—D. Gabrielle Phelan
*Attorney, Agent, or Firm*—Gary Bond; Monsanto Company; Arnold, White & Durkee

[57] ABSTRACT

A method and device for implanting large diameter objects subcutaneously or into the peritoneal cavity of bovines employs a beveled, puncturing, but substantially non-incising trocar.

10 Claims, 13 Drawing Sheets

U.S. PATENT DOCUMENTS

| | | | |
|---|---|---|---|
| 2,519,555 | 8/1950 | Fields | 128/266 |
| 2,572,155 | 10/1951 | Hoyt | 128/272 |
| 2,587,364 | 2/1952 | Mitchell | 128/217 |
| 3,016,895 | 1/1962 | Sein | 128/217 |
| 3,140,078 | 7/1964 | Krahe et al. | 259/47 |
| 3,141,583 | 7/1964 | Mapel et al. | 222/309 |
| 3,144,178 | 8/1964 | Sarnoff | 222/327 |
| 3,256,884 | 6/1966 | Hill et al. | 128/235 |
| 3,348,545 | 10/1967 | Sarnoff et al. | 128/218 |
| 3,506,008 | 4/1970 | Huck | 128/261 |
| 3,620,216 | 11/1971 | Szymanski | 128/217 |
| 3,760,804 | 9/1973 | Higuchi et al. | 128/260 |
| 4,154,239 | 5/1979 | Turley | 128/217 |
| 4,403,610 | 9/1983 | Lodge et al. | 604/61 |
| 4,452,775 | 6/1984 | Kent | 424/19 |
| 4,492,576 | 1/1985 | Dragan | 433/90 |
| 4,557,724 | 12/1985 | Gregonis et al. | 604/49 |
| 4,576,604 | 3/1986 | Guittard et al. | 604/890 |
| 4,624,847 | 11/1986 | Ayer et al. | 424/15 |
| 4,670,249 | 6/1987 | Ivy et al. | 424/424 |
| 4,721,612 | 1/1988 | Janoff | 424/1.1 |
| 4,723,958 | 2/1988 | Pope et al. | 604/890 |
| 4,725,439 | 2/1988 | Campbell et al. | 424/449 |
| 4,769,011 | 9/1988 | Swaniger | 604/218 |
| 4,786,501 | 11/1988 | Janski | 424/422 |
| 4,787,384 | 11/1988 | Campbell et al. | 128/330 |
| 4,816,439 | 3/1989 | Jorgensen | 514/12 |
| 4,820,267 | 4/1989 | Harman | 604/60 |
| 4,834,268 | 5/1989 | Keller | 222/327 |
| 4,846,793 | 7/1989 | Leonard | 604/62 |
| 4,857,534 | 8/1989 | Croom, Jr. et al. | 514/299 |
| 4,863,901 | 9/1989 | Wilmore | 514/12 |
| 4,891,208 | 1/1990 | Janoff | 424/1.1 |
| 4,917,685 | 4/1990 | Viswanathan et al. | 604/891.1 |
| 4,923,096 | 5/1990 | Ennis, III | 222/391 |
| 4,941,874 | 7/1990 | Sandow et al. | 604/60 |
| 4,959,218 | 9/1990 | Eckenhoff et al. | 424/473 |
| 4,973,304 | 11/1990 | Graham et al. | 604/48 |
| 4,997,825 | 3/1991 | Wagner | 514/171 |
| 5,034,229 | 7/1991 | Magruder et al. | 424/422 |
| 5,035,897 | 7/1991 | Ayer et al. | 424/473 |
| 5,037,420 | 8/1991 | Magruder et al. | 604/892.1 |
| 5,045,082 | 9/1991 | Ayer et al. | 604/892.1 |
| 5,057,318 | 10/1991 | Magruder et al. | 424/438 |
| 5,059,423 | 10/1991 | Magruder et al. | 424/438 |
| 5,091,185 | 2/1992 | Castillo et al. | 424/438 |
| 5,100,392 | 3/1992 | Orth et al. | 604/175 |
| 5,110,596 | 5/1992 | Magruder et al. | 424/438 |
| 5,112,614 | 5/1992 | Magruder et al. | 424/422 |
| 5,135,523 | 8/1992 | Magruder et al. | 604/892 |
| 5,137,727 | 8/1992 | Eckenhoff | 424/422 |
| 5,156,851 | 10/1992 | Castillo et al. | 424/497 |
| 5,162,116 | 11/1992 | Shepherd | 424/438 |
| 5,174,999 | 12/1992 | Magruder et al. | 424/423 |
| 5,180,591 | 1/1993 | Magruder et al. | 424/473 |
| 5,209,746 | 5/1993 | Balaban et al. | 604/892 |
| 5,219,572 | 6/1993 | Sivaramakrishman et al. | 424/438 |
| 5,223,266 | 6/1993 | Eckenhoff et al. | 424/473 |
| 5,227,167 | 7/1993 | Carr et al. | 424/438 |
| 5,232,708 | 8/1993 | Castillo et al. | 424/497 |
| 5,234,692 | 8/1993 | Magruder et al. | 424/473 |
| 5,234,693 | 8/1993 | Magruder et al. | 424/473 |
| 5,234,694 | 8/1993 | Magruder et al. | 424/473 |
| 5,238,687 | 8/1993 | Magruder et al. | 424/473 |
| 5,281,197 | 1/1994 | Arias et al. | 604/57 |
| 5,292,307 | 3/1994 | Dolzine et al. | 604/54 |
| 5,304,119 | 4/1994 | Balaban et al. | 604/51 |
| 5,312,333 | 5/1994 | Churinetz et al. | 604/57 |
| 5,329,616 | 7/1994 | Magruder et al. | 604/892.1 |

OTHER PUBLICATIONS

R. J. Early, et al., Growth and metabolism in somatotropin–treated steers: III Protein synthesis and tissue energy expenditures. J. Animal Science 1990 68: 4153–4166, Abstract . . . .

Colin J. Peel, et al., Effect of exogenous growth hormone on lactational performance in high yielding dairy cows. J. Nutr. 111:1662–1671, 1981, Abstract . . . .

L. D. Sandles, et al, Growth and carcass composition of pre–pubertal dairy heifers trated with bovine growth hormone. Animal Prod. 1987 44: 21–27 Abstract . . . .

B. H. Breier, et al., Influence of nutritional status and oestradiol–17β on plasma growth hormone, insulin–like growth factors–I and –II and the response to exogenous growth hormone in young steers. J. Endocr. (1988) 118, 243–250, Abstract . . . .

B. H. Breier, et al., The somatotrophic axis in young steers: influence of nutritional status and oestradiol–17β on hepatic high–and low–affinity somatotrophic binding sites. J. Endocr. (1988) 116, 160–177, Abstract . . . .

Endopath Tristar Trocar Package Graphics 1993.

Endopath Tristar Trocar Advertising Mailer 1992.

Proceedings, Scientific Seminar on Development in Korea, Efficacy and Safety of Bovine Somatotropin in Holstein and Hanwoo pp.1, 70–88, May 24, 1994.

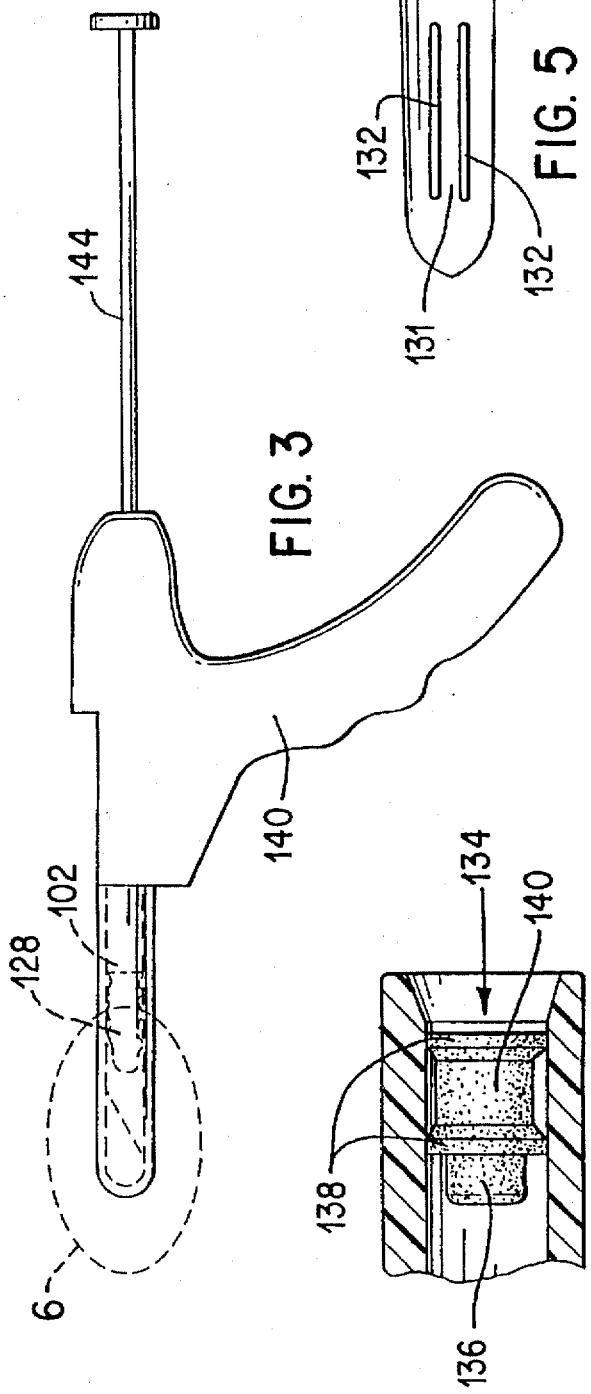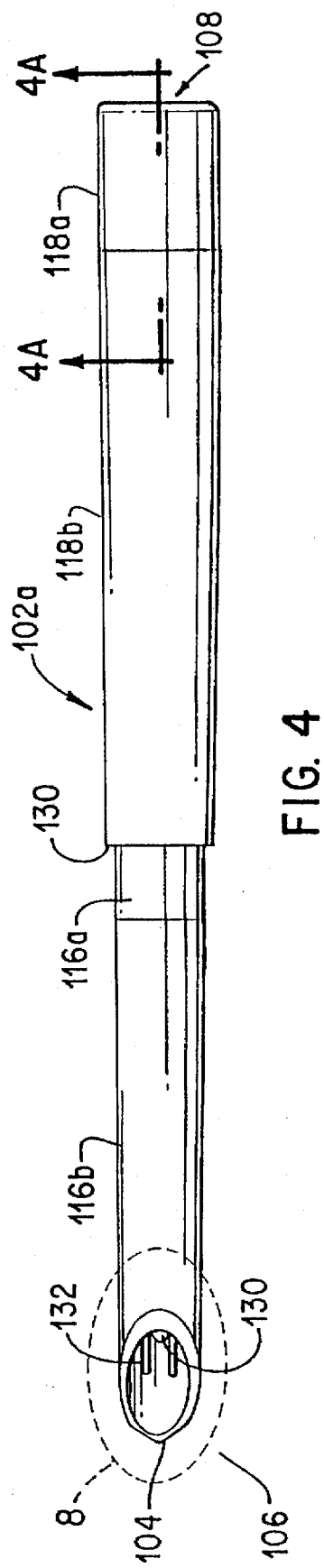

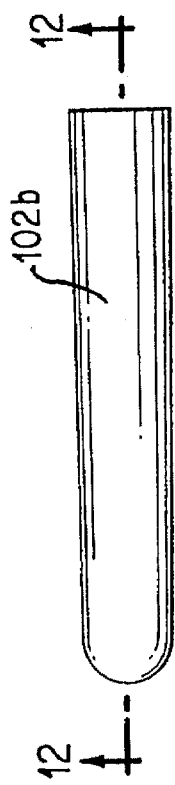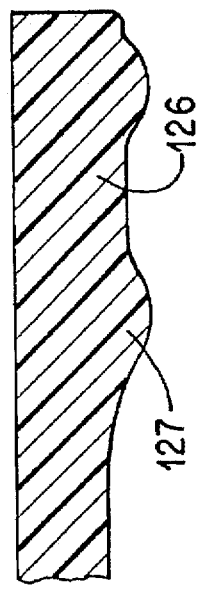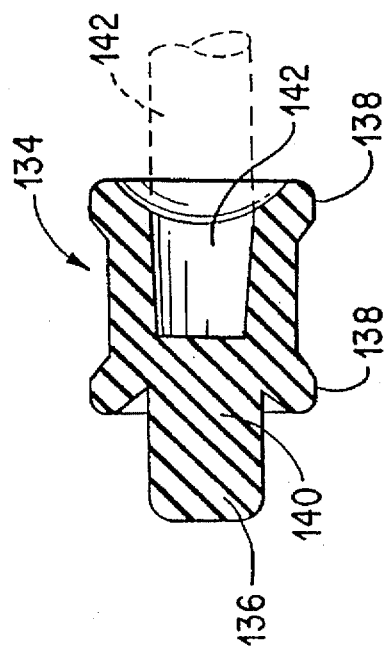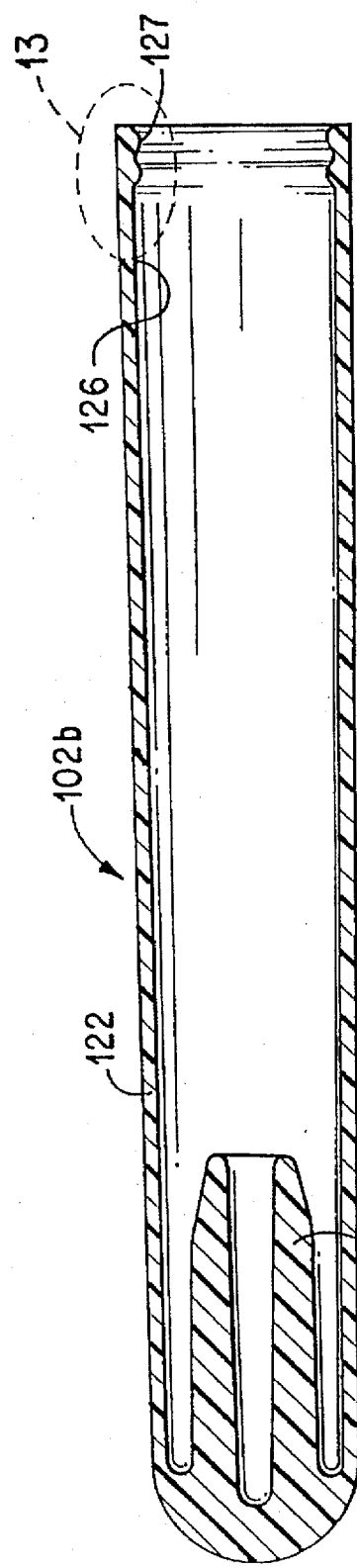

5,670,162

METHOD AND DEVICE FOR IMPLANTATION OF LARGE DIAMETER OBJECTS IN BOVINES

This application is a divisional of U.S. Ser. No. 08/270,196 filed Jul. 1, 1994, now pending.

FIELD OF THE INVENTION

The invention relates to method and device for implantation of large diameter devices or capsules in bovines. In one aspect, the invention relates to a method of implantation which is effective and from which the bovine readily heals. In another aspect, the invention relates to a device specifically adapted for intraperitoneal implantation in bovines which can be used in such a method.

SETTING OF THE INVENTION

In the field of raising cattle for dairy products and meat, it is sometimes desirable for various reasons to implant a large diameter object subcutaneously or in the intraperitoneal cavity of the bovines. For example, in preparing finishing beef cattle for slaughter, it may be desired to insert a prolonged release device or capsule or pellet into the intraperitoneal cavity to enhance average daily gain, body weight, carcass weight, dressing percentage and the like. As another example, in enhancing milk production in dairy cattle, it may be desirable to implant such devices or capsules or pellets subcutaneously such as described in Supplemental Exemplary Embodiment A and Supplemental Exemplary Embodiment B. It may also be desirable to implant large diameter devices such as temperature monitors and other electronic instrumentation, animal identification transponders, and the like. Many other large diameter devices will occur to those skilled in the art.

Such devices or capsules or pellets in order to provide a suitably prolonged release and to be readily visible after the slaughter Of the animal may be of substantial size. However, feedlot operators and technicians and cattle and dairy farmers are reluctant to undertake such treatment with large diameter objects, although advantageous and economically beneficial, unless it can be accomplished readily, without significant injury to the bovine, requires minimal care, and suitably heals. Thus, implantation of large diameter objects presents a significant problem to animal husbandry and also to the providers of treatments and devices for cattle.

The prior art has dealt with devices for injection of liquids into the peritoneal cavity and with trocars for relieving bloating of the rumen. The rumen is the first division of the stomach of a ruminant animal, distended into the peritoneal cavity, in which food is partly digested before being regurgitated for further chewing.

The prior art has also dealt with devices for subcutaneous implantation of pellets. The pellets are generally of relatively small diameter and the implanters generally have hide-incising tips which, if they were made larger and came into contact with underlying tissues, would cause relatively extensive bleeding and damage. Moreover, coring of the hide and underlying flesh could result, facilitating peritonitis if such materials were discharged into the peritoneal cavity, and generally impeding healing.

SUMMARY OF THE INVENTION

In accordance with the invention, a method is provided for implanting large diameter objects in the intraperitoneal cavity of bovines which can be accomplished readily, without significant injury to the bovine, requires minimal care after implantation, and suitably heals.

The method comprises providing a generally cylindrical large diameter object with an outside diameter in the range of about 8 to about 15 millimeters (mm). An incision is made in the hide of the left paralumbar fossa of the bovine, the incision having an orientation and length and depth such that gaping of the resulting wound substantially does not occur after inserting an object therethrough. A generally cylindrical tube having an external diameter of less than about 25 mm for passing through the opening and having an internal diameter for passing the large diameter objects therethrough and having a non-hide-incising tip effective for penetrating underlying tissues and for puncturing the peritoneum and a length for extending through the incision, the underlying tissues and into the peritoneal cavity, is inserted into the incision, and is caused to puncture and penetrate the peritoneum, and the large diameter objects are inserted therethrough. The tube is removed and the incision in the hide closes.

In accordance with a further aspect of the invention, there is provided a device for the subcutaneous or intraperitoneal implantation of large diameter substantially size-invariant objects into a bovine. The device comprises a plastic tube having an outside diameter of less than about 25 mm and an inside diameter effective for passing therethrough objects having an outside diameter in the range of about 8 to about 15 mm. A first end of the tube is beveled and has a non-hide-incising tip effective for penetrating tissues underlying an incision in the hide and for puncturing the peritoneum. Adjacent the first end is means for releasably retaining large diameter objects in the tube while the tube is inserted into the incision in the bovine's hide. Adjacent the second end is a slidable seal which can be urged to deliver the large diameter objects within the tube past the releasing means and out of the first end of the tube.

In accordance with another aspect of the invention there is provided a disposable administration package or article of manufacture for intraperitoneal administration of a beneficial agent to a bovine. The article comprises a disposable plastic tube having a non-hide-incising tip at a first end, the tip being effective for penetrating bovine tissues underlying an incision in the hide and being effective for penetrating the intraperitoneal cavity of the bovine. A plastic sheath sterilely encloses a first portion of the tube adjacent a first end, the first portion having a length effective for extending from left paralumbar fossa of a bovine into the intraperitoneal cavity. Retaining means is provided adjacent the first end for releasably retaining objects within the tube after the sheath is removed. The tube encloses one or more osmotically-driven pumps having an outside diameter of about 8 to about 15 mm for delivery of a beneficial agent. A seal adjacent the second end of the tube completes sterile or low bioburden enclosure of contents of the tube.

BRIEF DESCRIPTION OF THE DRAWINGS

The invention will be further understood and appreciated from the following detailed description and the drawings in which:

FIG. 3 is a schematic illustration of a device for implanting large diameter objects mounted in a gun for administering the implants, all in accordance with the invention.

FIG. 4 illustrates the exterior appearance of a device in accordance with the invention.

FIG. 4A is a longitudinal section along the line 4A—4A in FIG. 4.

FIG. 5 is a detail drawing showing the appearance of the obverse side of the tip of the device of FIG. 4.

FIG. 10 illustrates a longitudinal section through a seal adjacent the second end of an embodiment of the invented trocar.

FIG. 11 illustrates the exterior appearance of cap 102b.

FIG. 12 illustrates an axial longitudinal section along the line 12—12 in FIG. 11.

FIG. 13 illustrates in detail the region identified as 13 in FIG. 12.

Figure 1:
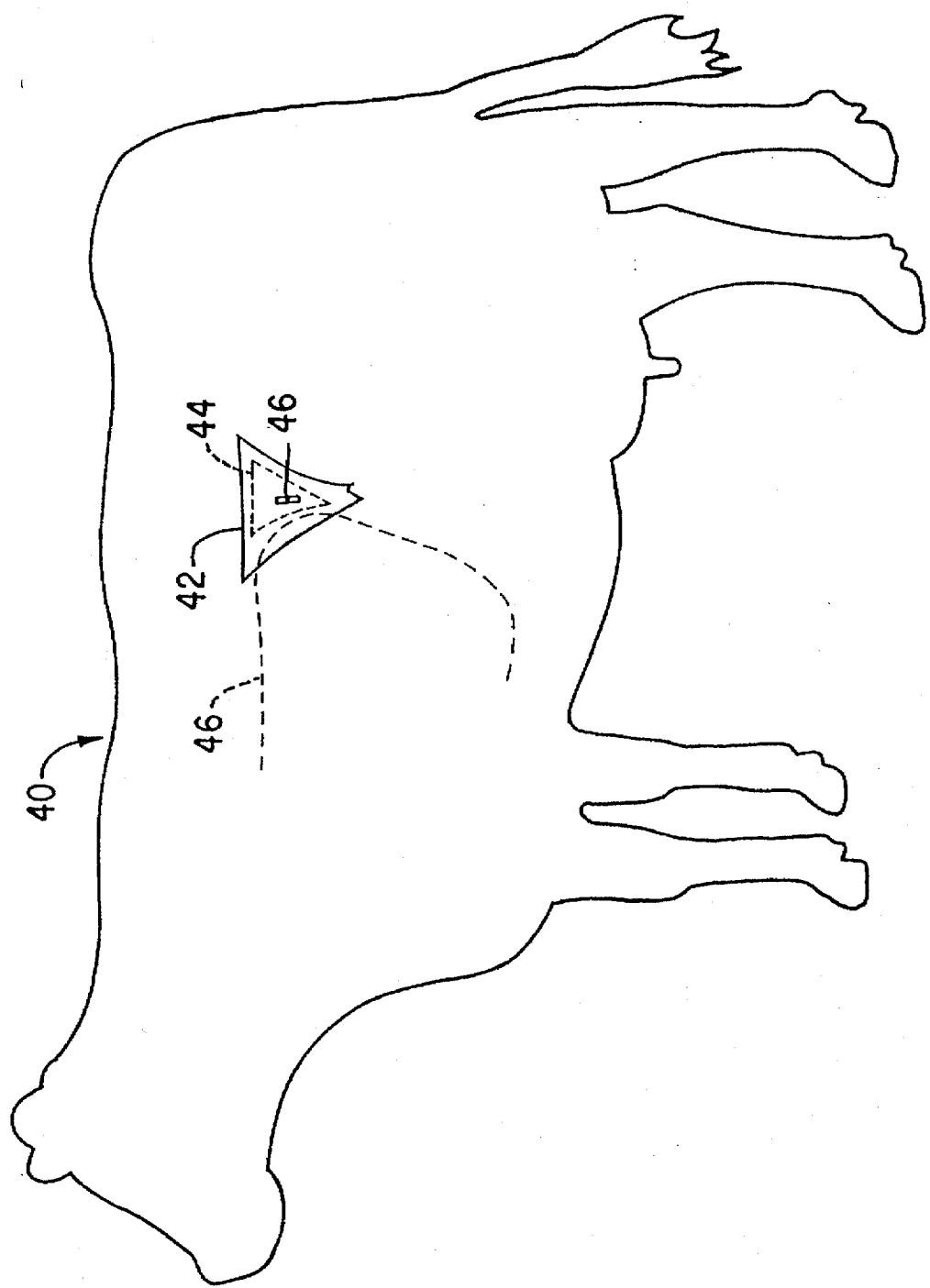
FIG. 1 is a line drawing of the hind portion of a bovine showing a typical arrangement of left paralumbar fossa, an adjacent portion of the intraperitoneal cavity, and the rumen.

The invention will now be described in detail showing preferred embodiments of the invention, but is not limited thereto, but by the claims appended hereto interpreted in accordance with law.

DETAILED DESCRIPTION OF THE INVENTION

In accordance with the invention, a method is provided for implanting large diameter objects in the intraperitoneal cavity of bovines which can be accomplished readily, without significant injury to the bovine, requires minimal care after implantation, and readily heals.

The method comprises providing a generally cylindrical size-invariant large diameter object with an outside diameter in the range of about 8 to about 15 mm. The objects can be, for example, capsules, pellets, mechanical or osmotic pumps for delivering beneficial agents, electronic identification devices and monitors, and the like. As used herein, size-invariant refers to an object whose diameter does not significantly alter during implantation, for example, by crushing or otherwise. In a preferred embodiment, the objects are osmotic pumps for the delivering of a beneficial agent such as described in Supplemental Exemplary Embodiment A.

The minimum outside diameter of the large diameter objects in accordance with the invention is about 8 mm since it has been found that such devices can be made effective for delivering a beneficial agent over a prolonged length of time, and can be readily identified at the time of slaughter. The maximum outside diameter in accordance with the invention is about 15 mm since larger diameter objects require an incision in the hide of the animal greater than about 20 to 25 mm in length and it has been determined that when the incision is less than this range that substantial sealing of the wound occurs rapidly, often within 15 minutes or less of implantation, so that mechanical force is required to reopen the incision, and very low incidence of injection site responses is observed. Further the peritoneal wound also effectively heals and when low bioload or sterility of the device is maintained little or no peritonitis other than localized non-septic peritonitis has been observed. See Examples 1 and 2 below.

In accordance with an aspect of the invention, an incision is made preferably vertically, in the hide of the left paralumbar fossa of the bovine, the incision having a length of less than about 20 to 25 mm such that gaping of the resulting wound does not occur after inserting an object therethrough and the wound readily seals. Preferably the incision is vertical relative to the ground, only in the hide, and substantially not in the underlying muscle layers which are more highly vascularized, thus minimizing bleeding. Controlled incision is also preferable because to the extent the underlying muscle tissues are incised, gaping of the wound is more likely to occur at shorter lengths of incision due to symmetrical destruction of the underlying tissues. The incision can be made by means known in the art such as scalpel, laser, and the like.

In accordance with the invention, large diameter substantially size-invariant objects are provided for intraperitoneal implantation. Such objects can be, for example, pellets or capsules of bovine somatotropin, of estrogen, or other metabolic regulators or drugs, or electronic devices and monitors. For example, the objects can be appropriately sized bovine somatotropin pellets as disclosed in U.S. Pat. No. 5,091,185. Alternatively and preferably, such objects can be devices for delivering bovine somatotropin and/or estrogen at a pulsatile or substantially constant rate such as described in Supplemental Exemplary Embodiment A and Supplemental Exemplary Embodiment B. Most preferably the objects are osmotic pumps such as are described in Supplemental Exemplary Embodiment A.

In accordance with a preferred embodiment of the invention, a disposable plastic generally cylindrical tube having an external diameter of less than about 25 mm, for example 20 mm, for passing through the incision and having an internal diameter for passing the large diameter objects therethrough and having a substantially non-hide-incising tip effective for penetrating underlying tissues after the incision has been made and for puncturing the peritoneum and having a length for extending through the incision, the underlying tissues and into the peritoneal cavity, is inserted into the incision, is caused to penetrate the underlying tissues and to puncture and penetrate the peritoneum, and the large diameter objects are inserted therethrough. Preferably the length inserted into the bovine is sterile prior to use.

As used herein, plastic according to its general technical usage refers to a high polymer, usually synthetic, optionally combined with other ingredients such as curatives, fillers, reinforcing agents, colorants, plasticizers, and the like, which can be formed or molded under heat or pressure in its raw state and machined to high dimensional accuracy, trimmed and finished in its hardened state.

The puncturing non-incising tip is beveled or slanted to facilitate passage through underlying tissues, but is substantially non-incising to reduce cutting or coring or both of the underlying tissues. Use of a beveled, mostly non-incising tip to pass through the muscle layers results in tearing, rather than incision, of the muscles; and damage to vascular structure and bleeding is reduced and healing facilitated because of quicker clotting and other factors. Preferably the bevel is less than 35° since 40° and 45° bevels cannot efficiently be urged through underlying tissues. 30° is much better than 35°, while 25° is only marginally better than 30°. To minimize length of the trocar it is preferred that the bevel be in the range of about 25° to about 35° relative to the horizontal axis.

The peritoneum is the serous membrane lining of the abdominal walls (parietal peritoneum) and investing the viscera (visceral peritoneum). The parietal peritoneum is the membrane which lines the abdominal and pelvic walls and the undersurface of the diaphragm. The visceral peritoneum is the membrane reflected at various places over the viscera, forming a complete covering for the stomach, spleen, liver, ascending portion of the duodenum, jejunum, ileum, transverse colon, sigmoid flexure, upper end of the rectum, uterus, and ovaries; it also partially covers the descending and transverse portions of the duodenum, the cecum, ascending and descending colon, the middle part of the rectum, the posterior wall of the bladder, and the upper portion the vagina. The peritoneum serves to hold the viscera in position by folds, some of which form the mesenteries, which connect portions of the intestine with the posterior abdominal wall; others form the omenta, folds attached to the stomach, and still others, the ligaments of the liver, spleen, stomach, kidneys, bladder, and uterus. The space between the parietal and visceral peritoneums is the peritoneal cavity, which consists of the pelvic peritoneal cavity below and general peritoneal cavity above. The general peritoneal cavity communicates by the foramen of Winslow with the cavity of the great omentum, which is also known as the lesser peritoneal cavity. As used herein, intraperitoneal cavity includes any of the pelvic peritoneal cavity, the general peritoneal cavity, and the lesser peritoneal cavity. More preferably, the implant is inserted into the lesser peritoneal cavity.

It has been discovered that access to the peritoneal cavity in bovines is best gained through the left paralumbar fossa in bovines which have been fasting or feed-restricted as discussed below. Initially, it was thought that insertion through the right paralumbar fossa would be the preferred side, as the rumen is positioned adjacent the left paralumbar fossa, and it was desired to avoid the possibility of damage to the rumen. However, the kidneys and associated kidney fat are asymmetrically distributed in the bovine toward the right side of the body and interfere with access to the peritoneal cavity on that side and further require a longer tube for implantation to assure that the implants are discharged into the intraperitoneal cavity and not into kidney fat or kidney where ineffective release or damage to the animal would occur. For this reason access to the intraperitoneal cavity in accordance with the invented method is accomplished through the left paralumbar fossa.

Referring to FIG. 1, the left paralumbar fossa is a generally triangular area 42 of about 6–8 inches diameter on bovine 40 between the hip bone 44 and the last rib and below the loin area on the left side. Tissue and hide depth here is typically about 0.5 to 2.0", hence tubes used for intraperitoneal implantation can be generally on the order of 1 to 5 inches or longer. The insertion depth of the tube needs to be greater than the actual thickness of the paralumbar region due to the potential for stretching of the peritoneal lining. As indicated above, the only internal organ presenting a risk of injury via the left paralumbar fossa is the rumen 46, provided the trocar is not pointed upward toward the kidney.

Damage to the rumen can be eliminated or reduced by applying the invented method to animals whose rumen is not too much distended into the target peritoneal cavity, for example, to fasting or feed-restricted animals. Preferably animals treated in accordance with the invented method have been fasting or feed restricted (reduced feed or water-only) for 6 to 24 hours, most preferably about 10 to 18 hours prior to administration since it has been observed that the rumen is typically flaccid or at least not typically distended into the implantation area at this time facilitating avoidance of injury.

After implantation, the specified incision in the hide (See reference numeral 46 is FIG. 1), which is preferably vertical to facilitate closure and to prevent pooling of blood and fluids during closure, is often already undergoing sealing and closure in 15 minutes to 1 hour so that force would have to be applied to reopen the incision. Investigation of the length of incision has shown that so long as the length is less than about 25 mm, more preferably, less than about 20 mm, this rapid sealing phenomenon is observed. Likewise, examination of bovines following slaughter has shown that they are overwhelmingly free of signs of peritonitis other than localized non-septic peritonitis.

Figure 2:
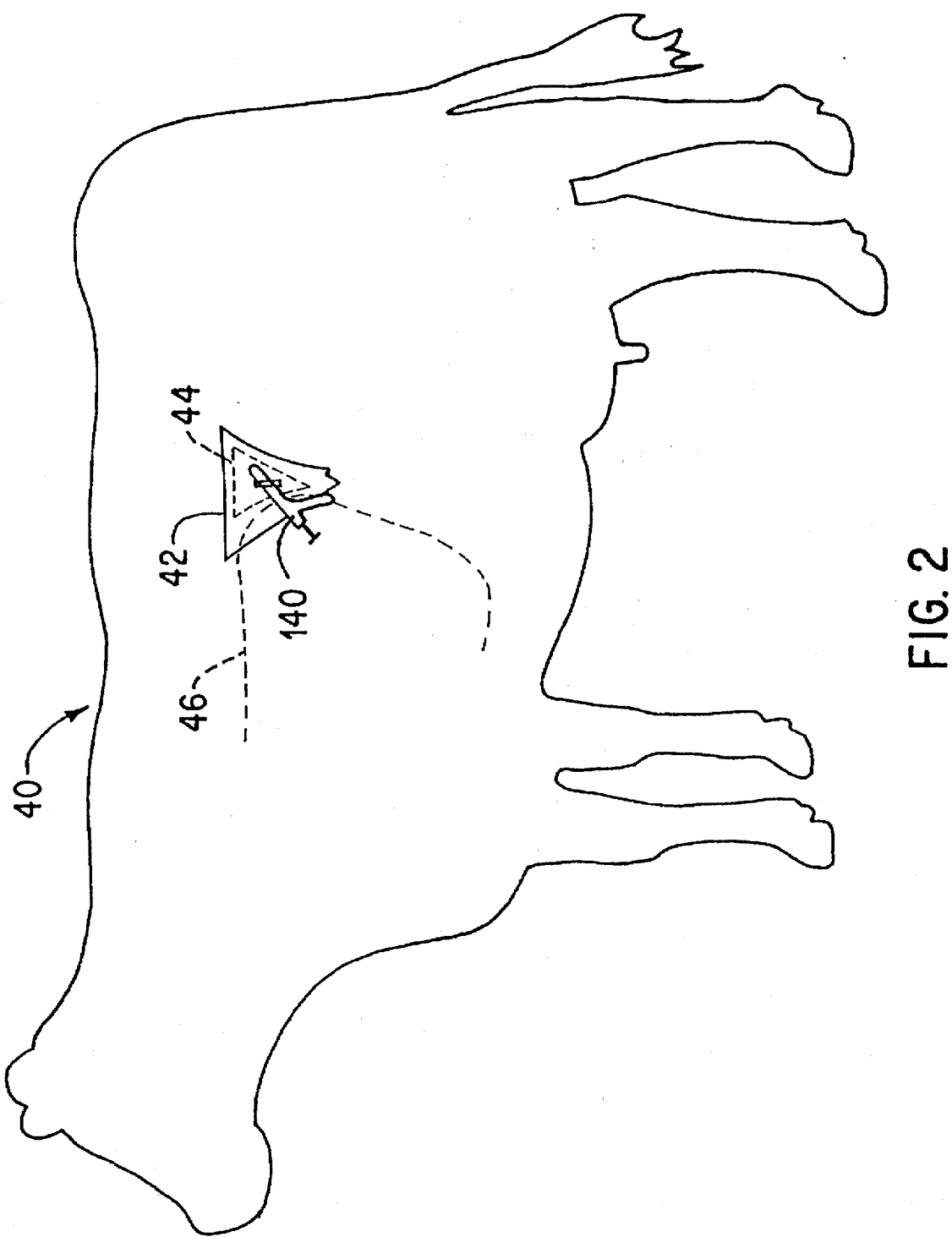
FIG. 2 is a modified FIG. 1 showing an incision made in the hide of the bovine and a device in accordance with the invention inserted into the opening and through the peritoneum into a portion of the peritoneal cavity.

The invention can be further illustrated by reference to the Figures, particularly FIGS. 1 and 2, wherein reference numeral 40 indicates the left paralumbar region of a bovine 42, reference numeral 44 indicates the targeted portion of the peritoneal cavity, 46 indicates the adjacent rumen, and 48 illustrates a vertical incision in the left paralumbar fossa. Referring now to FIG. 2, FIG. 2 further shows administration gun 140 having device 102 mounted therein inserted into the targeted peritoneal cavity 44.

Thus, in accordance with the invention, a method has been provided for implanting large diameter objects in the intraperitoneal cavity of bovines which can be accomplished readily, without significant injury to the bovine, requires minimal care after implantation, and rapidly heals.

In accordance with another aspect of the invention, there is provided a device for the intraperitoneal implantation of large diameter size-invariant objects into a bovine.

The device preferably comprises a plastic tube having an outside diameter of less than about 25 mm, preferably less than about 20 mm, and an inside diameter for passing therethrough large diameter size-invariant objects having an outside diameter in the range of about 8 to about 15 mm. In a first portion of its length which can be sized to extend from hide to intraperitoneal cavity in a bovine, the outer surface of the first portion is preferably sterile prior to use. A first end of the tube adjacent the first portion is beveled and has a puncturing but substantially non-hide-incising tip having a hardness and stiffness effective for puncturing the peritoneum. Adjacent the first end is means for releasably retaining the large diameter objects in the tube while the tube is inserted into an incision in the bovine's hide. Adjacent the second end is a slidable seal which can be urged to deliver the large diameter objects within the tube past the releasing means and out of the first end.

Referring now to FIG. 3, FIG. 3 illustrates administration gun 140 having package 102 mounted therein. Gun 140 has push rod 142 which can be used to deliver implants 128 as hereinafter described.

Referring now to FIG. 4, package 102 comprises trocar 102a and its contents hereinafter described and sheath 102b. Reference numeral 102a indicates a generally cylindrical plastic tube of unitary construction having an outside diameter of less than about 25 mm and an inside diameter capable of receiving generally cylindrical size-invariant objects having an outside diameter in the range of about 8 mm to about 15 mm.

As illustrated, the generally cylindrical plastic tube 102a may overall slightly taper distally, as illustrated, from right to left, sufficient to facilitate molding and mold-release of the device. The sidewall thickness of the device can also narrow distally as best illustrated in FIG. 13. The device is of a moldable or machinable plastic, preferably a moldable plastic having a hardness such that a tip 104 can be molded or machined tip effective for puncturing the peritoneal membrane but is otherwise substantially non-incising. Alternatively, a puncturing tip may be attached to the tube after construction or during molding. The generally cylindrical tube can be made of any non-toxic plastic which has appropriate strength, moldability, stiffness and, optionally, low moisture transmission rate. Thus the generally cylindrical tube can be polycarbonate, polyvinylchloride, acrylonitrile-butadiene-styrene (ABS), and the like. ABS is preferred because of its strength, moldability, stiffness and low moisture transmission rate, for example, Lustran® ABS available from Monsanto Company, St. Louis, Mo. The trocar can have a slight taper on both the interior and exterior sidewall to facilitate molding. Preferably, however, there is no taper of the interior diameter where seal 134 (See FIG. 4A) is seated adjacent the preferably chamfered second end as illustrated by reference numeral 118a; nor preferably is there taper of the exterior diameter in portion 116a, adjacent shoulder 120, where the sheath seals to the tube.

Device 102 comprises a first end 106 and a second end 108. First end 106 has a tip 104 which can be formed by double-beveling the tip of the tube, as illustrated. Generally, as discussed above, the primary bevel 110 is in the range of about 20 to 35 degrees, while the secondary bevel 112 (See FIG. 8) is in the range of 30 to 40 degrees measured as the angle between the bevel and a plane perpendicular to the longitudinal axis of the trocar, for example 34 degrees. Preferably, as illustrated, the bevels are selected to minimize the length of device 102 while providing a suitable puncturing tip. The inside surface or heel of tube 102, as illustrated at 115 in FIG. 6, can be rounded slightly to minimize roughness and the tendency to scrape and carry flesh, hair, and the like as device 102 is inserted into the flesh of an animal. The lower surface of the tip, as best illustrated by reference numeral 150 in FIG. 7, can be angled, for example, at about 5° relative to a longitudinal axis, to reduce thickness of the puncturing tip.

As illustrated, device 102 consists of first and second body portions 116 and 118 respectively, having substantially the same or slightly distally tapering inside diameters and different outside diameters forming a shoulder 120 therebetween. Shoulder 120 can be used to receive and seat the sheath, discussed below, and also to gauge or limit insertion of device 102 into a bovine after the sheath is removed.

Alternatively, the outside diameters can be the same. The length of the first portion from shoulder 120 to tip 104 is preferably sufficient to extend from the hide to the peritoneum of a bovine at the left paralumbar fossa. Thus, this length can be on the order of 1 to 5 inches. 4 inches has been found to be effective for puncturing the peritoneum even with a relatively inefficient tip. With a more efficient tip a lesser length of the first portion will be advantageous. Longer lengths can also be used.

As illustrated, a closed cap or sheath 102b having a coaxial tubiform spacer 124 molded in the tip thereof and having a generally cylindrical wall 126 is inserted on the first portion 116 maintaining the outer surface sterile before use. Spacer 124 has a length for ensuring that implants 128 do not rest on protuberance 130 while cap 102b is on device 102. As illustrated, molded sealing rings or annular ridges 127 of wall 126 (See FIGS. 12 and 13) rest against shoulder 120. Cap 102b is preferably constructed of an elastomeric material such that the annular rings will snuggly but removably engage portion 116a of trocar 102a. Sheath 102b can be molded of any plastic which has suitable moldability and pliability to allow for maintaining a sterility and/or moisture seal when installed on device 102. Optionally, the plastic can have a low moisture transmission rate. A preferred plastic is a polypropylene, for example, one having the characteristics of Himont PD626 available from Himont, Wilmington, Del. The length of the sheath is determined by the length of the device 102 which will be inserted into contact with bovine tissues, i.e., the combined length of 116a and 116b. The sheath can be slightly tapered so as to facilitate mold-release and to avoid a vacuum when sheath 102b is removed from device 102.

According to the invention, means is provided adjacent the tip for releasably retaining implants 128 within device 102 when the cap is removed and device 102 is held vertically. Many suitable means will occur to those skilled in the art. Preferably the means is of a type which can be molded and is made of the same material as device 102 since this simplifies manufacture. In the illustrated embodiment, the means comprises a bump or convex protrusion 130 (See FIGS. 4, 6, 7, and 8) which is molded on the interior sidewall of portion 116b on a flexible strip 131 (See FIGS. 5 and 8) bounded by longitudinal slits 132 passing through the sidewall. When cap 102b (See FIG. 9) is removed and implant 128 is urged, as hereinafter described, by push rod 142 toward tip 102, the pressure exerted by the implant 128 on protuberance 130 will cause strip 133 (See FIG. 6) to bow outwardly permitting passage of implants 128. When cap 102b is in place, for example during shipping and handling, spacer 124 maintains the implants away from protuberance 130. Thus cap 102b, spacer 124, and the retaining means cooperate to provide an effective, moldable device.

In the illustrated embodiment of FIG. 3, second portion 118, together with first portion 116, and cap 102b constitute device 102. The combined length of device 102 is determined by the length of portion 116 which will traverse the bovine from hide to peritoneal cavity and by the total length required for mounting in gun 140 and for enclosing a desired number of implants 128. Preferably, the number of implants 128 is a number that will be implanted in one bovine during one administration. This number may be 1, 2, 3, or more.

Adjacent the second end of device 102 is a seal 134 for sealing (best seen in FIGS. 4A and 10) and, in cooperation with cap 102b, for maintaining sterility of the interior of device 102. After insertion of seal 134 the tube 102 can be heat treated adjacent the second end to provide a stop ridge (not illustrated) holding seal 134 within tube 102. Preferably the seal is a molded plug comprising bumper 136, first and second side wall engaging members 138 and body 140. Preferably all parts are generally cylindrical but may be of different shapes effective for their respective purposes as will be apparent to those skilled in the art. The seal 134 preferably includes a generally cylindrical, preferably slightly frustoconical well 142 optionally radiused at its proximal end and narrowing distally therein, for engaging and being engaged by rod 142 to urge implants 128 past protuberance 130 and out of the first end 106 of device 102. The seal will engage rod 142 (See FIG. 5) which will preferably have a length and/or range of travel such that seal 134 cannot be expelled from the first end of device 102 during use. Preferably the point of contact between the rod and the piston is past the center point of the piston to limit the tendency for sealing edges to be deviated as the seal is advanced. Bumper or spacer 136 has a diameter less than the smallest diameter adjacent protrusion 130 and a length sufficient to ensure that implants 128 can be urged beyond a point of possible engagement with protrusion 130.

Seal 134 can preferably be molded from any suitable plastic or rubber such as a thermoplastic elastomer having suitable sealing and deforming characteristics, for example, the ability to produce a sterile and optionally a moisture seal along a device having a slight taper. Particularly preferred is Santoprene® 271-55 brand thermoplastic elastomer, available from Monsanto Company St. Louis, Mo., which is deformable but noncompressable under conditions of use, and has the ability to produce both sterility and moisture seals and to compensate for sidewall irregularities and taper. Other seals, such as seals using O-rings or fabricated of other materials can also be used.

Figure 6:
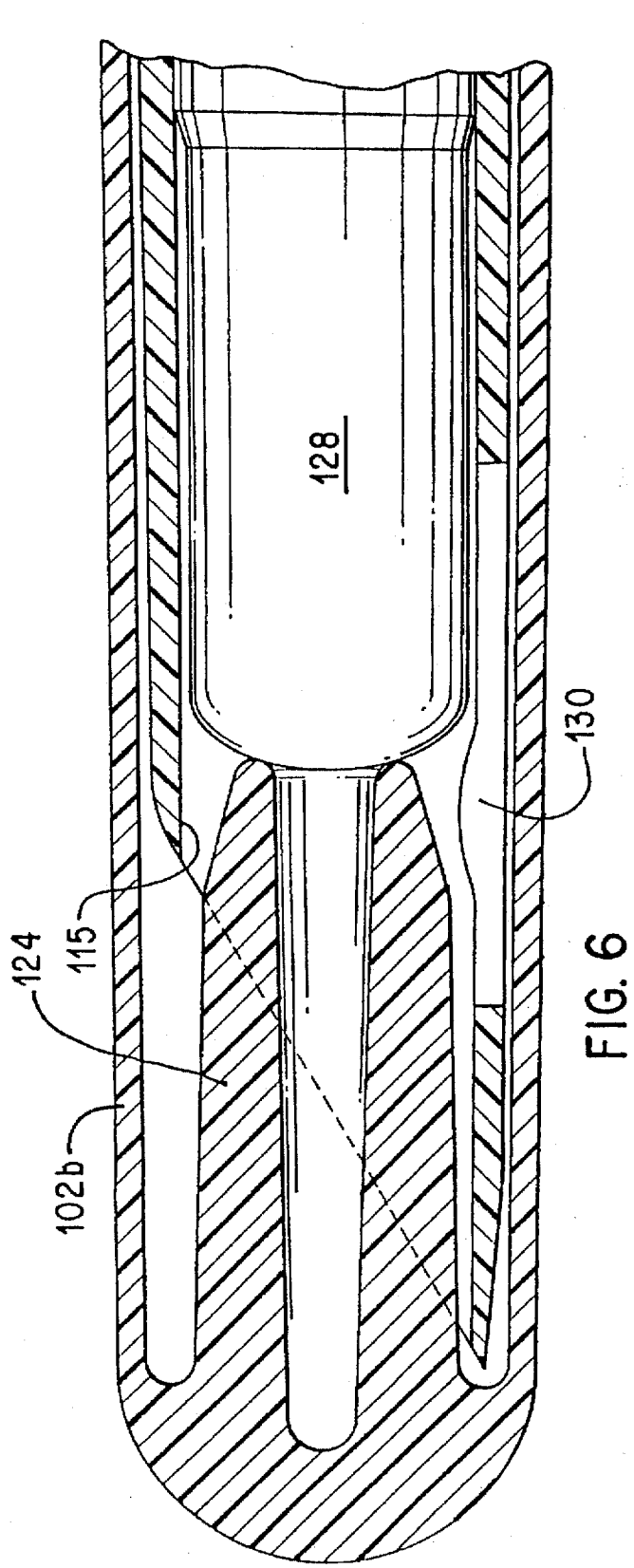
FIG. 6 is a longitudinal section of the portion designated 6 in FIG. 3.
Figure 7:
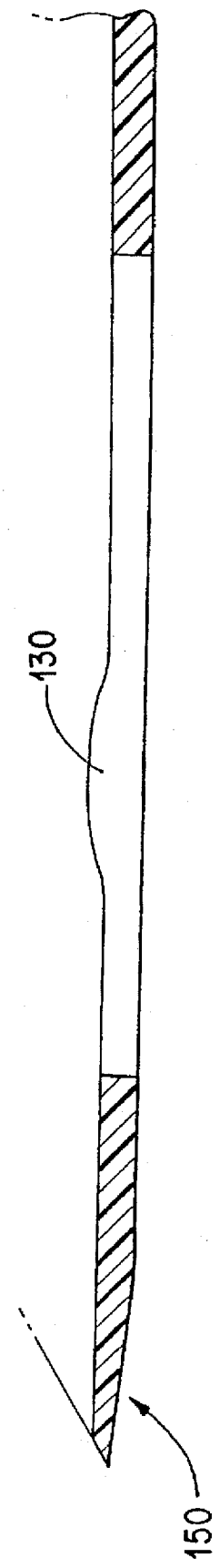
FIG. 7 is a detail drawing illustrating a longitudinal section through the tip of the invented trocar.
Figure 8:
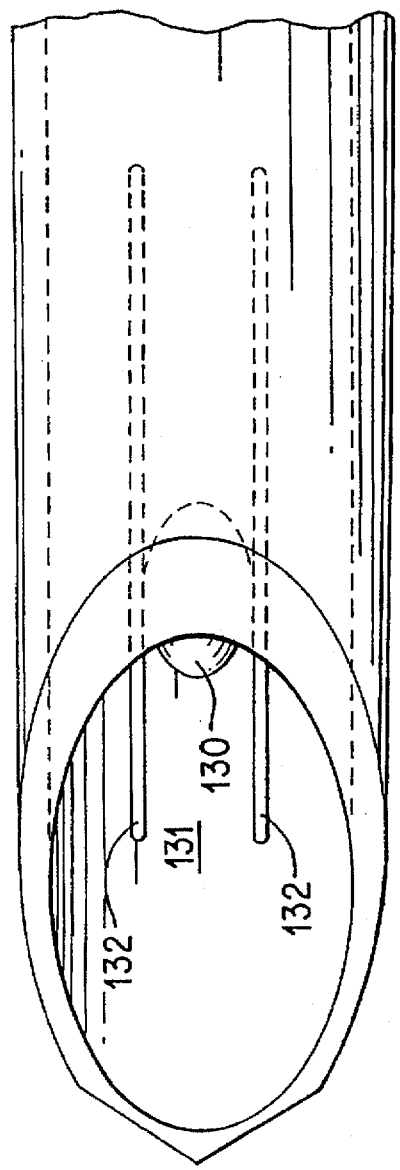
FIG. 8 is a detail drawing of the portion designated 8 in FIG. 4.
Figure 9:
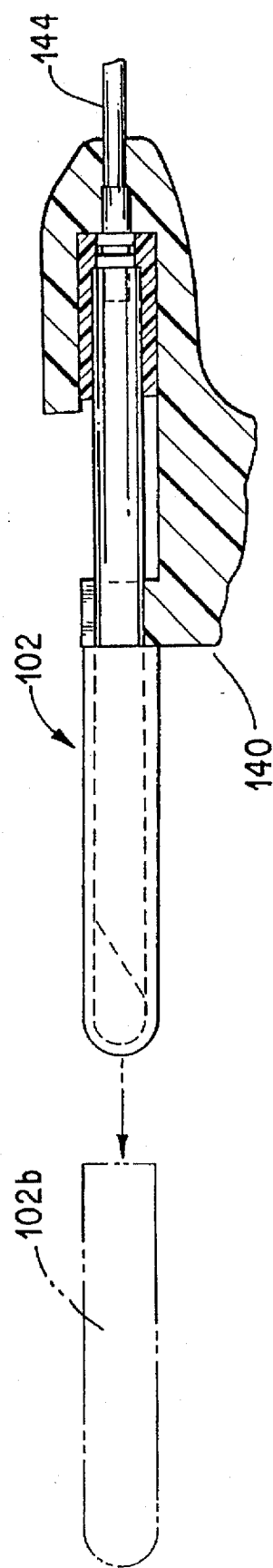
FIG. 9 illustrates removal of the sheath from the combined trocar and gun of FIG. 3.

Referring now to FIGS. 4, 5, 6, 7 and 8, these Figures illustrate the positioning of strip 133, bounded by slits 131, and having protuberance 130 thereon, in a preferred embodiment of the device. As illustrated, this type of retaining means, which can be included in a mold for device 102, is positioned on the side of tube 102 having the greatest length. In this way, it is insured that slits 131 are adjacent to but do not open onto tip 104 where the openings could snag tissue and carry hair and other contaminants into the bovine. As best illustrated in FIGS. 4, 6 and 8, protuberance 130 is preferably positioned opposite or counter to the shortest length of tube 102. In this way implants 128 are maintained in the sterile interior environment of tube 102 until use, and the overall length of 102 can be kept to a minimum. Other retaining means are known to those skilled in the art and may be used such as, for example, those disclosed in U.S. Pat. Nos. 2,587,364 incorporated herein by reference, O-rings, and the like.

Referring again to FIGS. 3 and 9, these Figures illustrate a device 102 mounted in a gun 140 having a push rod 142. Such devices are well-known in general and it suffices to the person skilled in the art to point out that gun 140, adapted for device 102, should firmly grasp device 102 in such a way that cap 102b can be removed (See FIG. 9) after insertion in the gun and to minimize wobble during implantation. Further, push rod 142 should have a length and/or range of travel such that seal 134 of device 102 cannot be expelled from first end 106.

Figure 14:
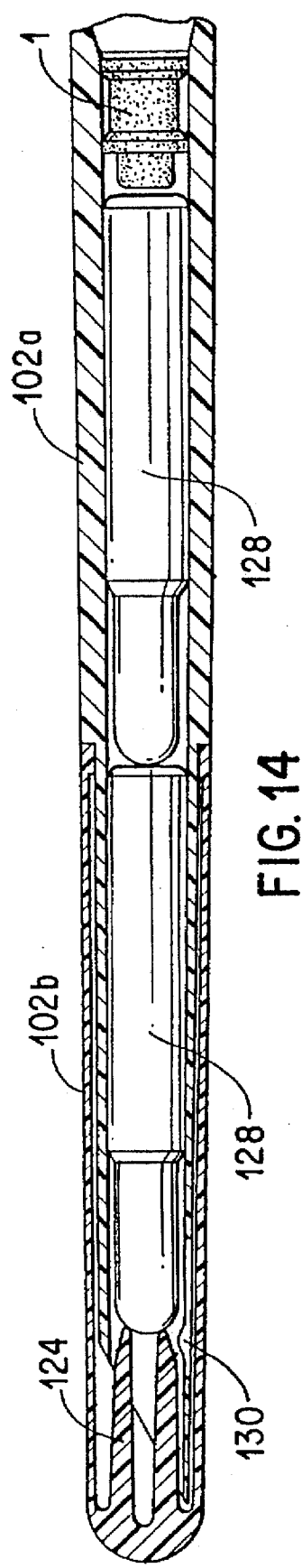
FIG. 14 illustrates a package in accordance with the invention.
Figure 15:
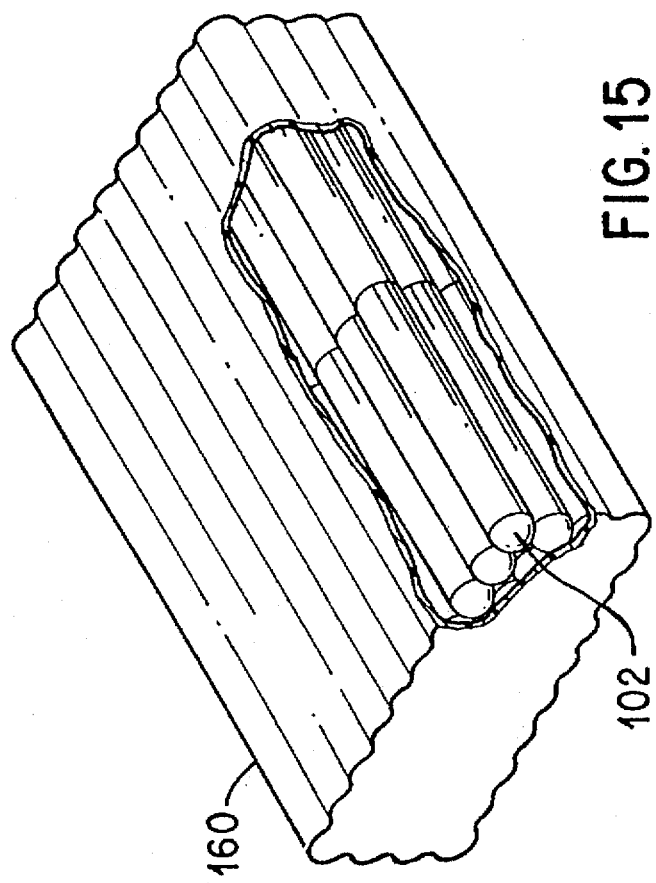
FIG. 15 illustrates a sealed package comprising a plurality of sterile packages in accordance with FIG. 3.

Referring now to FIG. 14, this Figure illustrates a package 102 in accordance with the invention comprising body 102a and closed sheath 102b and containing between spacer 124 and seal 134 two implants 128, such as, for example, bovine somatotropin implants described in Supplemental Exemplary Embodiment A. Conditions of manufacture and loading are such that implants 128, and the interior and exterior surfaces of device 102 are preferably of low bioload and more preferably sterile. It is also envisioned that device 102 can be constructed of materials which are substantially impermeable to water since, as described in Supplemental Exemplary Embodiment A, the osmotic implants may include salt tablets whose exposure to moisture prior to use would result in variable performance at startup. Alternatively, one or a plurality of devices 102 could be packaged in a water-impermeable material, such as foil 160, as illustrated in FIG. 15.

EXAMPLE 1

This example illustrates the significance of the incision in the hide being vertical and approximately 25, or 20 mm, in length or less.

Cattle were intraperitoneally implanted using a 12.6 mm outside diameter metal trocar inserted through an incision approximately 18–20 mm in length and vertical relative to the ground. On occasion animals have been checked after an incision was made. The time lapse would vary from approximately 10–60 minutes. In all instances the incision had completely closed and required that physical force be utilized to re-open the initial incision for trocar insertion. During implantations an effort is made to keep incisions less than approximately 25 mm in length and not to cut the muscle layers beneath. It has been observed that when incisions are greater than 25 mm or if the muscle layers are cut with a scalpel that the incision has the propensity to gap open after the trocar has been removed.

Histological examination has been performed on the scar left after implantation at 21 and 40 days post implantation. At 21 days, the lesion resembles a capital "T". The transverse upper portion of the "T" lies directly beneath the epidermis and extends laterally in each direction for approximately 1 mm. It consists of a dense wide band of highly cellular collagen, primarily fibroblasts. Occasional small pockets of inflammatory cells such as polymorphs and lymphocytes do not exceed a dozen or so cells. The inflammatory portion of the reaction period is well passed. The overlying epidermis is normal. The vertical portion of the "T" passes through the subcutaneous musculature in the form of nearly mature collagen containing occasional penetrating new vessels. Beneath the musculature the "T" extends outward as a web of similarly almost mature collagen.

At 40 days the epidermis is normal and intact. The only evident lesion consists of a narrow finger of mature collagen extending from the subcutis through musculature.

The epidermis was intact and normal in all animals indicating the sites would be difficult to detect grossly. Collagenous scar tissues was normal and had very limited numbers of inflammatory cells. The collagenous tissue still distinctly contained fibroblasts at 21 days and lesser numbers at 40 days indicating that the final shrinkage, as seen in mature scar tissue, was in progress.

EXAMPLE 2

This example illustrates that use of a low-bioburden device having an outside diameter of 25, or 20 mm, or less, does not result significantly in peritonitis in bovines, other than in localized non-septic peritonitis.

A series of trials were conducted with stainless steel trocars for insertion of non-sterile, low-bioburden 5, 8 and 10 mm osmotic implants dispensing solutions of bovine somatotropin (bST).

In the first set of trials, 5 mm osmotic implants dispensing bST at a rate of about 2 to 3 mg/d were implanted into the peritoneal cavity of 902 cattle. The trocar had an outside diameter of 7.1 mm and a maximum insertion length of about 9 cm. In the case of 672 of these animals, the animals received a second intraperitoneal implantation 42 days prior to slaughter; while the remaining 230 cattle received only one intraperitoneal implantation 42 days prior to slaughter. At slaughter there was a 3-5% incidence of localized non-septic peritonitis observed by the USDA Inspector-in-Charge; however implants were difficult to recover, in part due to their small size (5 mm) and to their lack of color (clear). No septic peritonitis was observed.

In the second set of trials 953 cattle were implanted intraperitoneally with non-sterile low-bioburden 8 mm, blue osmotic implants dispensing bST at a rate of about 6 to 9 mg/d. The trocar had an outside diameter of about 9.6 mm and a maximum insertion length of about 10 cm. The cattle were slaughtered about 90 days post-implantation. These implants were easier to recover and the incidence of localized non-septic peritonitis was comparable to that observed with the 5 mm osmotic implants. No septic peritonitis was observed.

In a third set of trials 1153 cattle were implanted with non-sterile 10 mm, blue, osmotic implants dispensing bST at a rate of about 6 to 10 mg/d. The trocar used for implantation had an outside diameter of about 12.6 mm and a maximum insertion length of 10 cm. The cattle were slaughtered 120 to 140 days post-implantation. In two of these trials, each with approximately 288 implanted cattle, the non-sterile implants had a relatively high bioburden and the incidence of adhesions between the parietal peritoneum and the visceral peritoneum and the incidence of localized peritonitis with a more severe appearance affecting larger areas of the peritoneum cavity was observed to have increased. The increased bioburden indicates the desirability of sterile or at least low bioburden implants to avoid higher levels of adhesions and increased severity of localized peritonitis. In subsequent trials with low bioburden 10 mm implants it has been observed this more severe form of localized peritonitis and the severity of adhesions has been reduced.

This Example illustrates that peritoneal implantation of low-bioburden implants reduces adhesions and does not result significantly in peritonitis in bovines other than in localized non-septic peritonitis. Use of sterile implants is expected to further decrease adhesions and further reduce the likelihood of septic peritonitis.

EXAMPLE 3

This example illustrates manufacture and assembly of the invented device. Device 102 is molded out of an acrylonitrile-butadiene-styrene (ABS)(Lustran® 248 brand ABS available from Monsanto Company, St. Louis, Mo.) plastic with a white or a gray colorant added for appearance and to serve as a light barrier. The device has an overall length of 8.97" from the tip of the bevel to end of the device that is inserted into a gun for delivery.

The bevel has an approximately 30° angle and has one bevel of 34° and a second bevel of 5°. The tip of the bevel has been given a sharp point to facilitate penetrating the peritoneum, however, the heel of the bevel is dulled or rounded to eliminate coring.

Internal diameter at the bevel is 0.424" and is 0.48" at the end in which the seal resides during storage, thus producing a taper to facilitate molding. In the area in which the seal resides there is no taper to assure a seal between the device sidewall and the sidewall-engaging portions of the seal while the device in storage. At the seal end of the device a chamfer (See FIG. 4A) facilitates loading of the implants and the seal.

At the end adjacent the beveled tip a retaining system incorporates a protuberance between two longitudinal slits 0.02" wide by 1.0" long. The protuberance begins to rise 0.66" from the tip of the device and is 0.021" above the inner diameter wall, thus reducing the opening from 0.424" to 0.407". The protuberance has a radius of 0.25" as the implant begins to be discharged over the protuberance and a radius of 0.40" as it passes from the protuberance. The first radius retains the implant and the second radius facilitates ejecting the part from molding. The retaining system incorporates the protuberance height and ability to flex via the two longitudinal slits. Hence, the implant in this example has an outer diameter of 0.41" and is retained until the implant is expelled past the protuberance causing approximately 0.003" deflection in the protuberance without causing damage to the exterior of the implant.

The outer diameter of the device consists of two different diameters. The bevel end is 3.97", the proximal 0.5 inch is not tapered, and will maintain a 0.56" outer diameter for providing a seal surface when the sheath is applied. This end will be covered by the sheath and will remain sterile until the time of use. The second diameter is 5.0" in length and the outside diameter is increased to 0.68" at the shoulder and is tapered to 0.77" at the second end. However, the last inch has no taper to facilitate mounting in the administration gun. An indicating mark is added to the outer diameter to show orientation of the bevel to the user.

Polypropylene (Himont PD626 available from Himont, Wilmington Del.) is used to mold the sheath and may or may not have a colorant added. The sheath covers the entire area that is to be inserted into the animal at the time of use. Total length of the sheath is 4.28" long and the outside diameter range from 0.61" at the closed end 0.68" at the open end. In the inside at the closed end is a protruding tubiform spacer long enough to keep the implant off of the protuberance during filling, shipping and storage.

In respect of the sheath, there are two proximal similar annular rings which rise 0.019" above the internal diameter of 0.6". Thus, a seal will be made between the trocar's outside diameters, of 0.561" and the inside diameter 0.558" of the sheath's sealing rings. A balance between the sterility seal and the removal force of the sheath is accomplished by the annular rings.

The seal is injection molded using Monsanto Santoprene and is 0.811" in length. There are two sidewall-engaging sealing rings with an outer diameter of 0.490" and which are 0.076" wide. The distal or front face of the seal has an extrusion or bumper of 0.273" long by 0.25 diameter that will insure that all implants have been pushed past protuberance 130 when the push rod has passed through its preferred range of motion. The seal has a hollow in its proximal end to accept a push rod of an administration gun to facilitate the seal's trueness as it travels down the interior of the device.

EXAMPLE 4

This example illustrates the invented method of the invention. The left paralumbar fossa is cleaned of debris, alternatively hair clipped, and a 20 mm vertical incision is made to a depth required to pierce the hide (about 7-10 mm). The slit is placed preferentially in the exact center of the fossa, but may also be to areas caudal to this site. A disposable trocar is inserted through the slit, with the primary direction being perpendicular to the skin. Inclining the trocar during insertion is not recommended due to the possibility of injury to the loin area and/or possible implantation into kidney fat.

However, the trocar can be tilted once insertion is completed. A distinctive feel and/or sound can sometimes be detected by experienced technicians when the peritoneal lining yields to the trocar tip. The implants contained in the trocar are discharged to the peritoneal cavity and the trocar is withdrawn. The wound is permitted to heal with no additional attention or an antiseptic is applied to the surface of the wound.

SUPPLEMENTAL EXEMPLARY EMBODIMENT A

Osmotic Pump for Use With the Invention

In the following discussion, like reference numerals refer to like elements in the figures.

Figure 16:
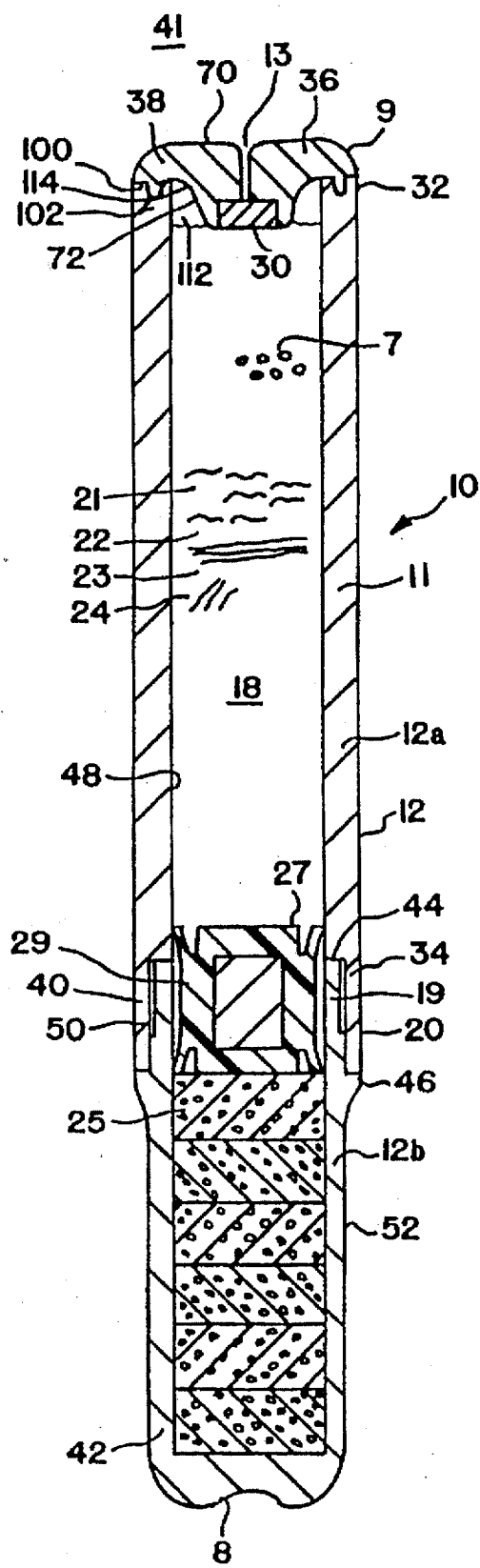
FIGS. 16–22 depict features of a preferred osmotic pump that can be implanted using the device of the instant invention.

FIG. 16 depicts in opened view one embodiment of a delivery device that may be used in accordance with the present invention. Delivery system 10 of FIG. 16 comprises a housing 11 formed of a wall 12, which wall 12 comprises a first wall section 12a and a second wall section 12b. Wall 12, comprising first wall section 12a and second wall section 12b, surrounds and defines an internal compartment 18. Delivery system 10 has at least one exit passageway 13 for delivering a beneficial agent 7 formulation from delivery system 10, the inlet of which is in contact with beneficial agent during storage and use. Optionally, the exit passageway can be occluded with a material like that in seal 30, discussed below, that gets discharged, leaches or erodes during the time of use. In FIG. 16, delivery system 10 comprises a dome-shaped rear end 8 and a flattened lead end 9. In embodiments not shown, delivery system 10 can be manufactured with a pair of rounded or flat ends 8 and 9. The term "lead end", as used herein, generally denotes the end from which beneficial agent 7 is released from the system. In use, either the lead end or the rear end may be implanted first.

Wall section 12a may be in the form of an tubular member having a first and a second open ends 32 and 34, respectively. In this particular embodiment, an enclosure means 36 is positioned on first wall section 12a at its lead end 9. In this particular embodiment, the enclosure means is in the form of an end cap 38. The wall section 12a and end cap 38 together form passageway 13, seal 30 and surround that portion of internal compartment 18 that contains a beneficial agent 7 formulation.

Referring now to FIG. 16, wall section 12b has a first or open end 40 and a second or enclosed end 42, the enclosed end at end 8 and the open end distant therefrom. Open end 40 defines and forms receiving means 19. Receiving means 19, having a first buttress 44 and second buttress 46, is received within enclosing means 20 of first wall section 12a. First buttress 44 can be formed by providing the enclosing means 20 of the first wall section 12a with a first interior surface portion 48 having a first inner or bore diameter and a second interior surface portion 50 having a second inner or bore diameter, so that the internal buttress or interior annular ledge 44 is formed or defined where the first and second interior surface portions of wall section 12a meet.

Formed on the outer surface 52 of the wall section 12b is the second buttress 46. Second buttress 46 is positioned to abut with the second open end 34 of the first wall section 12a when the enclosing means 20 of the wall section 12a abuts with the first buttress 44. As a result, the second buttress 46 in combination with the first buttress 44 forms a double butt joint to mate the wall sections 12a and 12b for a strong joint while minimizing the external discontinuities or surface friction of the implant device and providing a smooth transition between the first and second wall sections. In this particular embodiment, the portion of the second wall section 12b inserted within the first wall section 12a has the same thickness as that portion outside the first wall section. In addition, as a result of this construction, the inside surface of the first and second wall sections facilitates the travel of the piston along the formed smooth continuous interior surface.

Figure 20:
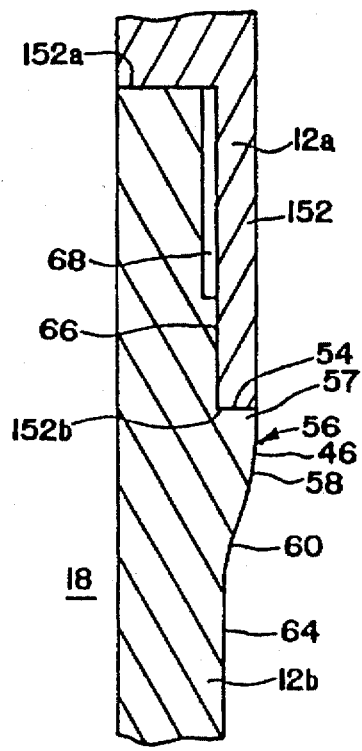

As best shown in FIG. 20, the buttress 46 includes a buttress engaging surface 54 for abutting with the first wall section 12a and an exterior or contoured surface 56 to smooth the transition from the exterior surface of the first wall section 12a to the exterior surface of the second wall section 12b. In the illustrated embodiment, when viewed in cross-section, has a generally s-shape. The contoured surface 56 includes a non-tapered annular portion 57, an annular convex portion 58 and a concave annular portion 60. As a result, the buttress 46 extends smoothly radially outward from the exterior surface of the second wall section to the exterior surface diameter of the first wall section, smoothing the transition between sections of the device having different outer diameters.

Wall section 12b surrounds that portion of internal compartment area 18 that contains a means 25 for expanding and for occupying space in compartment 18 for delivery of a beneficial agent formulation from delivery of a beneficial agent formulation from delivery system 10. The thickness and the surface area of the second wall section 12b contribute to the rate of passage of fluid through the membrane second wall section. In the preferred embodiment the second wall section is preferably formed in one piece from the water permeable material in the form of a membrane cup 12b, about 1.442 inches long, and inner diameter of about 0.288 inches. The second wall section 12b has an outer diameter of about 0.365 inches at the receiving end 19 and about 0.378 inches at the portion not inserted within first wall section 12a. A membrane cup of substantially these dimensions provides a desired fluid flow rate through the comprising the second wall section of about 10–15 mg $H_2O$/day and more particularly about 12–14 mg $H_2O$/day into contact with the expanding means 25 therein. The two wall sections, sections 12a and 12b, at receiving means 19 and enclosing means 20 are close in size. Wall section 12a and wall section 12b can be telescoped completely until halted by buttresses 44 or 46 into a closed and continuous internal walled position. In the illustrated embodiment, optionally, optionally, a plurality of longitudinal ribs 66 formed upon the outer surface of the second wall section on the lead end or side of the engaging wall 54, space apart the first and second wall sections to define and form adhesive receiving cavities 68 between the first and second wall sections and in between the longitudinal ridges. Optionally, the wall sections 12a and 12b can be held together by heat fusion, by an adhesive, or the like. Preferably the adhesive is a cyanoacrylate adhesive having a low-enough viscosity to wick into the joint and form a secure bond. A cyanoacrylate adhesive having the same qualities and characteristics as that sold by Permabond of National Starch and Chemical Company under the brand name Permabond USP Grade 701 Adhesive is sufficient. Buttresses 44 and 46 ensure that the juncture of 12a and 12b are smoothly and precisely joined in mated contact without discontinuities which would facilitate encapsulation of device 10.

Figure 18:
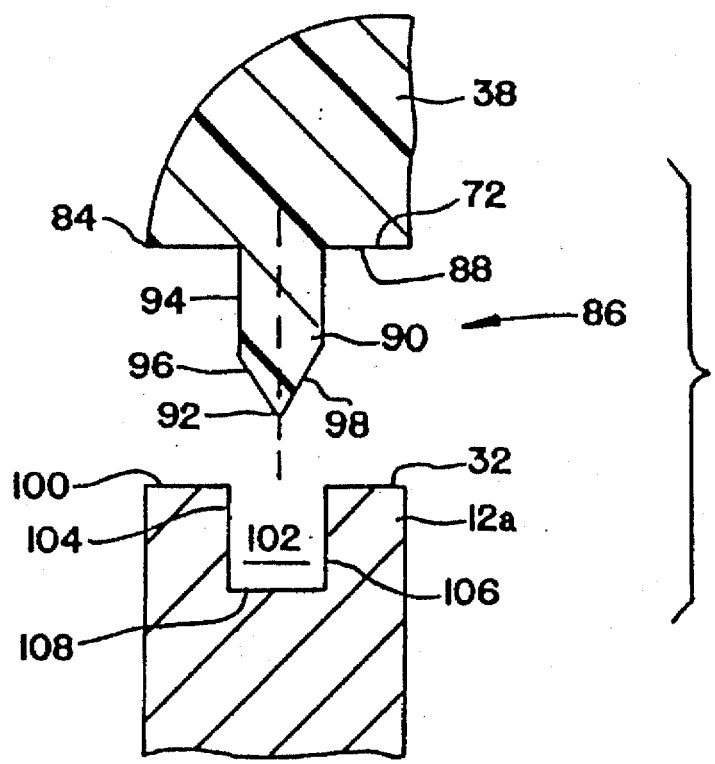

Referring again to now to FIG. 16, there is shown, as discussed in more detail with regards to FIG. 18, an embodiment of the mating end cap 38, adapting the end cap for ultrasonic welding to the first wall section 12a; and maintaining the exit passageway 13 in contact with the beneficial agent 7, while minimizing the dilution and/or degradation of the beneficial agent by adjacent body fluids present at the environment of use 41.

The end cap 38 is especifically beneficial when delivering fluid sensitive materials, protecting the material to be delivered before and after activation of the device. The exit port 13 is sized in diameter and length to provide a specific superficial formulation flow rate to eliminate dilution of the formulation by external fluids. The internal seal 30 provides point of use readiness without having to reopen the device, provides for a long term stability seal, protects formulation at start-up and has consistent rupture pressure to provide consistent startup. The end cap 38 also provides a headspace 112 forward of the formulation that acts to minimize internal pressure from thermal expansion of formulations while allowing the exit port 13 maintain contact with the formulation through all phases of the pump operation. The use of an end cap also facilitates automated Ultrasonic welding of the cap by protecting formulations during the welding process as a result of a melt sink aspect of the endcap.

Figure 17:
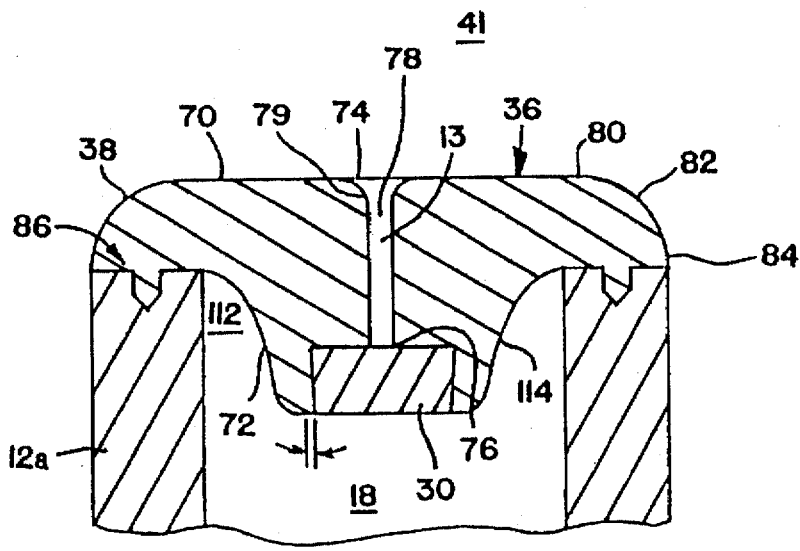

As best shown in FIG. 17, end cap 38 includes a first end cap side 70, a second end cap side 72 and an exit passageway 13 extending from the external environment 41 into internal chamber 18 and contacting formulation 7. Exit passageway 13 is designed for an adequate formulation flow rate, driven by fluid swellable driving member 25 and a partition member 27 including piston 29 to prevent dilution of the formulation in chamber 18 by the inflow of fluids from external environment 41. Exit passageway 13 is also maintains the pressure drop for a given rate of release of the formulation from device 10. Exit passageway 13 is preferably designed so that the rate of outflow of formulation exceeds the rate at which fluids from the external environment can diffuse inwards. The length of the exit passageway provides a means for compensating for slight variations in the efflux or outward flow rate of the beneficial agent. First side 70 includes an external face 80, the external face generally defining a plane substantially perpendicular to the longitudinal axis of the end cap 38. The communicating passageway 78 has a generally frustro-conically shaped contoured interior annular surface portion 79, smoothly joining the larger diametered first exit aperture 74 with smaller diametered communicating passageway 78 and second exit aperture 74.

Along its outer edge, the external face 80 joins with an annular concentric rounded portion 82 for rounding off the edges of the device.

As best shown in FIG. 18, second side 72 of end cap 38 also includes a mating portion 86 for engaging or mating with the first wall section 12a, adapted for ultrasonic welding. The mating portion 86 includes an annular mating surface 88 on the second side 72 for engaging with the first wall section 12a, and a tenon 90 extending outward therefrom towards the first wall section 12a.

As earlier described, first wall section 12a includes first open end 32. The open end 32 has an engaging surface portion 100 for engaging with the end cap 38. This surface or open end 100 defines a mortise 102 for receipt of the tenon 90 extending outward from the mating surface 88 of the end cap 38. In one particular embodiment, the mortise is defined by a first mortise wall 104, a second mortise wall 106 and a mortise bottom wall 108.

Referring again to FIG. 17, it can be seen that end cap 38 is adapted with an inward extending portion 110 which defines a headspace 112 between wall 12a and end cap 38. Headspace 112 remains untilled with formulation 7 after chamber 18 is filled with beneficial agent formulation 7. In this way, regardless of the orientation of device 10, beneficial agent formulation is in contact with seal 30 or with exit passageway 13 and entrance of fluid into chamber 18 from external environment 41 is inhibited. The air confined within the head space 112 also allows for differential expansion of beneficial agent and plastic within the interior chamber 18.

Figure 19:
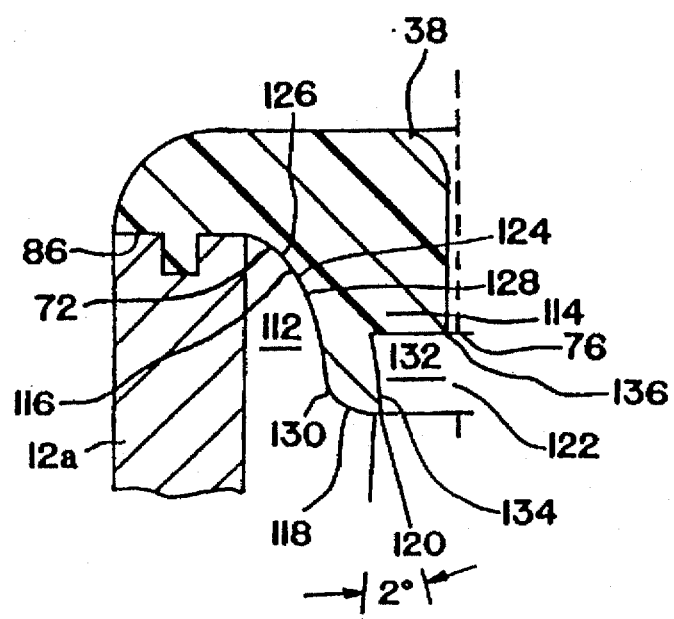

As best shown in FIG. 19, second side 72 of end cap 38 also includes an extension 114 for sealing the exit passageway 13 and maintaining the exit passageway in contact with the beneficial agent 7 disposed within a portion of the internal chamber 18. The extension 114 includes a generally cylindrical portion 116, extending outward and integral with the annular mating portion 86 such that when the end cap 38 is mating with the first wall section 12a. The extension portion 114 at its terminal portion 118 includes an end cap apex 120. Apex 120 includes or defines therein a depot 122 for receipt of a sealant. A sloping contoured surface 124 extends and connects the annular mating surface 80 with the depot 122. In one embodiment, the sloping surface 124 is generally s-shaped in cross-section and includes a first concave annular portion 126, a second concave annular portion 128, and a convex annular portion 130 forming a generally s-shaped surface in cross-section. In one preferred embodiment, the first concave annular portion 126 has a slope generally defined by a radius of about 0.029 inches from a center 0.125 inches radially outward from the central longitudinal axis and 0.083 inches along the central longitudinal axis from the apex 120 on second side 72. The second concave annular portion 128, integral with and extending radially inward from the first concave annular portion 126, joins with the convex annular portion 130, and has a slope generally defined by a radius of about 0.125 inches from a center at 0.200 inches radially outward from the central longitudinal axis and 0.026 inches along the central longitudinal axis from the apex 120 on the second side 72. The convex apex portion 130.

Depot 122 is comprised of the apex 120 defining a depot bore 132, for receipt of the sealant 30, the depot bore in fluid communication with the interior chamber 18 and the exit passageway 13.

In the handling and operation of the device, the relationship between headspace 112, depot 122 and exit passageway 13 plays a significant role. Headspace 112 permits contraction and expansion of the formulation 7 in device 10 during shipping and handling and also provides for the buildup of pressure in device 10 after implantation into an animal. Headspace 112 insures that any air left in the formulation is not in the formulation where it can form a bubble adjacent to exit passageway 13 but is confined to head space 112. If a bubble were permitted to form adjacent exit passageway 13, then when pressure built up sufficient to expel the plug in depot 122, an inflow of fluid from the external environment could dilute the formulation and the rate of delivery of formulation from device 10. In filling the device, heat treatment after filling assists in "setting" the formulation, locking the air bubble into place in headspace 112 where it will not affect initial operation of device 10.

Figure 21:
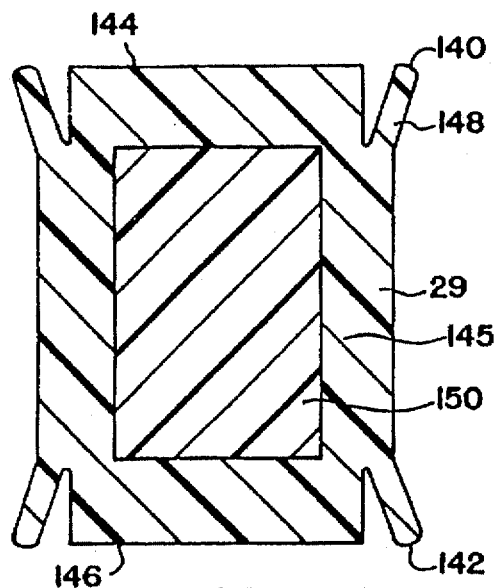

FIG. 21 illustrates in greater detail piston 29 of FIG. 16. Piston 29 is an elastomeric piston generally cylindrical in shape which incorporates first and second deformable seals 140 and 142. Piston 29 provides a high interference seal with minimum lateral force applied to the device wall which would impede longitudinal travel of the piston. The deformable seals 140 and 142 compensate for any irregularities in the internal wall of device 10 to provide an effective seal. The piston material, in one preferred embodiment, can be formed of any of four grades of Santoprene® 271 material, the most preferred grade being 271-55.

Figure 22:
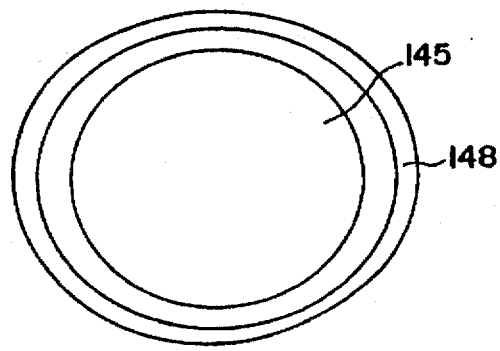

In one embodiment, the piston 29 includes a cylindrical body portion 145 positioned within the first wall section 12a. The piston 29 includes the cylindrical first or central body member 145 with first and second piston ends 144 and 146 respectively. The deformable seals 140 or 142 are formed at first and second piston ends 144 and 146 respectively. In one particular embodiment, the deformable seals 140 and 142 include a flared, conical skirt member or section 148. As best shown in FIGS. 21 and 22, the skirt 148 extends radially outward from the central body member 145 to terminate at a position spaced apart therefrom. Referring again to FIG. 21, a metal location detection member 150 is formed within the central cylindrical body member 145. The skirt member 148, extends radially outward at an oblique angle plane generally defined by the surface of the central body member 145. As a result, the distal end of the piston 29 are biased radially outward when articulating within the inner diameter of the first wall section 12a. The thickness of the skirt enables the skirt to provide sufficient wiping pressure to the inside surface of the first wall section without invoking such pressure as to cause the skirt to fold over.

Referring again to FIG. 20, first wall section 12a at its end distant from lead end 9 defines and forms an open end having a circumference for forming a lap joint 152 with wall section 12b. Second wall section 12b defines rear end 8 and it surrounds that portion of internal compartment 18 which initially contains an expandable driving means, here illustrated by expandable driving members 25a-f. Second wall section 12b at its end distant from rear end 8 defines and forms an open end having a circumference for forming lap joint 152. Second wall section 12b is adapted with buttress 56 for strength and precision of manufacture. Preferably the buttress is shaped to provide a smooth surface transition between wall sections 12a and 12b to minimize irritation leading to encapsulation.

Lap joint 152 includes, in the illustrated embodiment, lap joints 152a and 152b, reciprocally received one within the other for mating engagement when the two edges are assembled together. The lap joints 152a and 152b are of such a design as to provide a strong mechanically and hydrostatically intact seal when they are bonded together with an adhesive, such as a pressure-sensitive contact adhesive, a moisture-curing adhesive, an ultraviolet-curing adhesive or the like. While FIG. 16 shows the two wall sections assembled with the lap joint 152a of first wall section 12a enclosing the outside of the lap joint 152b of second wall section 12b, this arrangement is not critical and may be reversed. However, the illustrated embodiment is preferred since it provides additional restraint on the second wall section or membrane cup 12b pulling away from the lap joint. In addition, if the material used in the formation of the wall section surrounding the osmotic driving member, for example wall section 12b, is not as strong as the material used in the formation of the portion surrounding the beneficial agent 7, for example first wall section 12a, then the weaker material is preferably positioned or disposed to the inside or inserted within the stronger material. For example, if cellulose acetate butyrate is used for the portion surrounding the osmotic driving member and polypropylene is used to surround the beneficial agent 7, then the cellulose acetate butyrate wall is preferably on the inside of the polypropylene wall.

In a presently preferred embodiment, the exit passageway 13 and depot 122 are occluded with a material such as wax that gets discharged, leaches or erodes when placed in the organic environment of use. The implant can be implanted into the peritoneal cavity using an implanter.

Generally, an implanter comprises a tubular member with a central longitudinal axial bore, a pointed, elongated, annular concavely beveled implanting end and an implant-charging end. The implanting end and the charging end communicate through a bore. A plunger adapted to be removably inserted in the bore is designed for slidable movement therein for applying the necessary force for implanting the implant. Alternatively, the implant can be surgically or subcutaneously implanted in the peritoneal cavity.

Referring again to FIG. 16, first wall section 12a comprises a composition that is substantially impermeable to the exchange of fluid, beneficial agent 7 and other ingredients contained in delivery system 10. Wall section 12a, in a presently preferred manufacture, is substantially impermeable to the ingress/loss of an external/internal fluid to serve as a means for substantially protecting a beneficial agent 7 that is sensitive to exterior fluid present in the environment of use. Wall section 12a substantially restricts and prevents fluid from passing through wall 12a and entering into compartment 18 in the region containing a beneficial agent formulation. In one particular embodiment, when used in conjunction with bovine growth factors, including bovine somatotropin, wall section 12a may be formed of a material which provides a reduced adherence of the beneficial agent 7 to the wall 12a. For example, the use of polypropylene in the construction of wall 12a will reduce the adherence of bovine somatotropin to the surface of wall 12a.

In the preferred embodiment, wall section 12a is formed of polypropylene because of its excellent low permeability to water and because of its low surface tension which facilitates non-adhesion of beneficial agent 7 to the internal surface as compared with other materials such as polycarbonates, which empirically appeared to result in increased bearding on the respective wall surface/beneficial agent interface, especially when the beneficial agent included bovine somatotropin. Preparing polypropylene for bonding preferably includes preparing the surface thereof to increase the likelihood of an effective seal. Those skilled in the art will recognize that this may be performed by various methods, a non-inclusive list includes, for example, by priming with a chemical primer, abrading or knurling the surface, treatment with plasma and the like.

Second wall section 12b is permeable to the passage of fluid in at least a portion and it is substantially impermeable to the passage of other ingredients contained in delivery system 10.

Wall sections 12a and 12b optionally comprise a plasticizer that imparts flexibility and workability to the wall. Wall 12, comprising sections 12a and 12b, is nontoxic and, in a preferred embodiment, it maintains its physical and chemical integrity; that is, wall 12 does not erode during the dispensing period.

Compartment 18 comprises a beneficial agent 7 formulation, which beneficial agent 7 formulation comprises a beneficial agent 7, identified by dots, and a pharmaceutically acceptable carrier 21, identified by wavy lines. The pharmaceutically acceptable carrier may include more than one ingredient, such as a buffer 22, identified by horizontal dashes; a pharmaceutically acceptable vehicle 23, identified by vertical lines; a pharmaceutically acceptable surfactant 24, identified by slanted lines; and other formulation ingredients, as are known in the art.

Compartment 18 further comprises an expandable means or expandable driving member 25 optionally comprising members 25a–f. Expandable driving member 25 optionally comprises an osmagent homogeneously or heterogeneously blended with binder to form expandable driving member 25.

Compartment 18 may optionally comprise a partition layer 27. Partition layer 27 may optionally include, as in this embodiment, a piston 29, discussed in more detail with respect to FIG. 20. The partition layer 27 may include a portion which may be positioned between the drive piston 29 and the expandable driving member 25. The partition layer may comprise a composition that is substantially impermeable to the passage of fluid, and it further may act as a seal and restrict the passage of fluid present in the expandable driving member into the beneficial agent 7 formulation. Piston 29, alone or in cooperation with other portions of the partition layer 27, operate to essentially maintain the integrity of the beneficial agent 7 layer and the driving member layer 25. Portions of the partition layer 27 acts also to insure that the expanding driving force generated by the expandable driving member 25 is applied directly against piston 29 and thus is exerted on the formulation in compartment 18.

In operation, as the expandable driving means 25 absorbs and imbibes fluid through fluid-permeable second wall section 12b from the environment of use, it expands and pushes against piston 29 causing piston 29 to slide inside compartment 18. The piston may be lubricated, for example, using a silicone lubricant having the same characteristics as DOW 360 medical fluid 1000 cs. Piston 29 moves towards exit passageway 13, driving the beneficial agent 7 formulation in chamber 18 through passageway 13 for delivering the beneficial agent 7 to the environment of use. Second wall section 12b is telescopically capped by the engaging first wall section 12a. The two sections can be joined together by adhesive bond or various techniques such as solvent weld, thermal weld, ultrasonic weld, spin weld, induction weld, mechanical lock or by similar welding or bonding operations which may also be used in appropriate cases.

Delivery device 10 in FIG. 20 further comprises lead end 9, rear end 8, internal compartment 18, beneficial agent 7, pharmaceutically acceptable carrier 21, pharmaceutically acceptable buffer 22, pharmaceutically acceptable vehicle 23, and a pharmaceutically acceptable surfactant 24. In addition, a salt such as NaCl or KCl may be present in amounts of 1–4% by weight to assist stabilizing the state of formulation.

In a presently preferred embodiment, delivery device 10 comprises a plurality of expandable means members 25a–f initially housed in second wall section 12b. This configuration is merely illustrative and there may be any number of driving means present. Generally, there are from one to six expandable driving members; however, this number is not controlling. The expandable driving members in a presently preferred embodiment are formed as depots or layers and comprise like or unlike compositions. For example, driving members 25a–f can be made as tablets comprising like osmopolymers or like osmagents, or they can comprise unlike osmopolymers or unlike osmagents, or one or more of the members can be a composition comprising an osmopolymer together with an osmagent. The members can be the same or they can be different.

Referring again to FIG. 16, end cap 38 further comprises a depot 122 in fluid communication between internal chamber 18 and exit s passageway 13. Depot 122 can receive a material which is discharged, leached or eroded away during use. Preferably the material is wax or another material which can be discharged and depot 122 is sized to provide for sufficient present to discharge the material through passageway 13. This material serves several purposes: it seals delivery device 10 to prevent premature delivery of a beneficial agent 7 from delivery device 10 and to prevent evaporation of carrier components such as water during storage, it helps maintain the clean or optionally sterile environment inside delivery device 10, and it protects the ingredients inside the delivery device from oxidation by air and also protects the beneficial agent 7 from dilution by body fluids following implantation. More particularly, the seal 30 consistently releases at the same pressure using a 145 A wax in an end cap construction as described elsewhere in this application. In one preferred embodiment, the seal 30 releases at a pressure greater than 5–10 psi, more preferably greater than about 9 psi.

First wall section 12a, which surrounds the internal space of compartment 18 initially occupied by the beneficial agent 7 formulation, comprises a composition that does not adversely affect the beneficial agent 7, the osmopolymer, the osmagent, other ingredients in device 1 0, the host, or the like. First wall section 12a comprises a composition comprising means that substantially limits or prevents the passage of an external fluid into device 10. The phrase, "substantially limits or prevents," as used herein, indicates the volume of external fluid passing through first wall section 12a is substantially negligible, that is, about zero up to about 1 mL per day (see example 2 discussed more fully elsewhere in this application). Typical compositions for forming first section 12a are discussed in U.S. Pat. Nos. 5,057,318 for example.

The second wall section 12b comprises a composition comprising means that aid in controlling fluid flux into the compartment area occupied by the expandable driving member 25. The composition is semipermeable; that is, it is permeable to the passage of external fluids such as water and biological fluids and it is substantially impermeable to the passage of beneficial agents, osmopolymers, osmagents, and the like. Typical compositions comprising semipermeable materials for forming wall 12b are known in the art, a non inclusive list includes the group consisting of a cellulose ester, a cellulose ether and a cellulose ester-ether, including, for example, cellulose acetate butyrate. These cellulosic polymers have a degree of substitution, D.S., on the anhydroglucose unit from greater than 0 up to 3, inclusive. By "degree of substitution" or "D.S." is meant the average number of hydroxyl groups originally present on the anhydroglucose unit comprising the cellulose polymer that are replaced by a substituting group. Representative fluid-permeable materials are discussed in U.S. Pat. Nos. 4,874,388, 5,034,229, and 5,057,318, for example. The amount of semipermeable materials presently preferred in wall 12b is from about 20% to 100%. In the presently preferred form, the wall is formed of polypropylene equivalent to medical grade polypropylene PD626 sold by Himont, because of its excellent low water transport qualities and the relative low surface tension relative to the beneficial agent 7 formulation as compared to other polycarbonates, especially when the beneficial agent is bovine somatotropin.

Representative materials that can be used to regulate further the fluid flux of wall 12b include materials that decrease the fluid flux and materials that increase the fluid flux of wall 12b. Representative materials optionally added to wall 12b for either decreasing or increasing the flux are presented in U.S. Pat. Nos. 5,034,229 and 5,135,523.

First wall section 12a and second wall section 12b optionally comprise a nontoxic plasticizer. Representative plasticizers suitable for forming wall 12a or wall 12b are well known in the art and examples are presented in U.S. Pat. Nos. 5,034,229 and 5,135,123.

Delivery device 10 in its compartment 18 can also comprise pharmaceutical carrier 21. Carrier 21 may optionally include viscosity modulating vehicles (23), buffers (22), surfactants (24), dyes, and other additives known in the art, examples of which are disclosed in U.S. Pat. Nos. 5,034,229 and 5,135,123 to comprise the beneficial agent 7 formulation.

In a presently preferred embodiment, the beneficial agent 7 is bovine somatotropin, in an amount of from about 25% to about 60% by weight (wt %) of the beneficial agent 7 formulation, preferably from about 30 wt % to about 45 wt %.

The expandable driving means 25 initially surrounded by second wall section 12b and operable for pushing the beneficial agent 7 composition 20 from delivery device 10 comprises, in a presently preferred embodiment, an osmopolymer. The osmopolymers interact with water and aqueous biological fluids and swell or expand to an equilibrium state. The osmopolymers exhibit the ability to swell in water and to retain a significant portion of the imbibed and absorbed water within the polymer structure. The expandable driving means 25 in another preferred embodiment comprises an osmagent. The osmagents are known also as osmotically effective solutes and they are also known as osmotically effective compounds. The osmotically effective compounds that can be used include inorganic and organic compounds that exhibit an osmotic pressure gradient across a semipermeable, i.e. a fluid permeable, wall. The expandable driving member 25 yet in another preferred embodiment comprises an optional osmagent dispersed within the osmopolymer. The osmagent or osmopolymer can comprise a tablet or a layer or can be pressed into second wall section 12b. The osmagent or osmopolymer can be in any suitable form such as particles, crystals, pellets, granules, and the like, when pressed into a tablet layer and into wall section 12b. Osmagents and osmopolymers are known to the art in U.S. Pat. Nos. 3,865,108, 4,002,173, 4,207,893, 4,327,725, 4,612,008, 5,034,229, and 5,135,123 for example.

Piston 29, positioned between the beneficial agent composition and the expandable driving member 25, is a means for maintaining the separate identity of the beneficial agent composition and the driving member, for transmitting the force generated by the driving member against the beneficial agent composition, and for substantially restricting the passage of fluid between the beneficial agent composition and the driving member.

End cap 35, illustrated in FIG. 16, by being impermeable to fluid, having a passageway whose diameter length of a sufficient diameter and length; and a sealant preventing passage therethrough up to a predetermined threshold pressure, providing protection for the fluid-sensitive beneficial agent. The end cap provides a means for simply and conveniently assembling the device and particularly for filling the device with internal components such as the driving members, the partition and the beneficial agent formulation. Materials for forming end cap 38 may be chosen from those materials useful in preparing impermeable first wall section 12a.

The terms "exit means" and "exit passageway", as used herein, comprise means and methods suitable for the metered release of the beneficial agent 7 from compartment 18 of delivery device 10. This includes maintaining sufficient efflux or outward velocity of the beneficial agent to prevent an inward flow of fluid from the external environment to dilute the beneficial agent formulation in the portion of the compartment comprised by the first wall section. The exit passageway 13 includes at least one passageway, orifice, or the like, through first wall section 12a for communicating with compartment 18. The expression "at least one passageway" includes aperture, orifice, bore, pore, porous element through which the agent can migrate, hollow fiber, capillary tube, porous overlay, porous insert, and the like. The expression also includes material that gets discharged, erodes or is leached from the wall in the fluid environment of use to produce at least one passageway in delivery device 10. The expression includes structural characteristics that concentrate stress at a precise point in the wall so that only a small amount of force will induce breakage in the wall, yielding a passageway through the wall from compartment 18 to the outside of the device. A passageway or passageways can be formed by the discharge, as a result of the pressure created by the expandable member for example, of a material such as a wax. The passageway can have any shape such as round, triangular, square, elliptical, and the like, for assisting in the metered release of beneficial agent from delivery device 10. Delivery device 10 can be constructed with one or more passageways in spaced-apart relations or more than a single surface of a dosage form. Passageways and materials, equipment and methods for forming passageways are disclosed in U.S. Pat. No. 5,034,229.

Delivery device 10 can be manufactured by standard manufacturing techniques. In one process, the first wall section 12a and the second wall section 12b are independently injection molded or extruded into the desired shape. Then, the first wall section 12a is filled with the beneficial agent composition. The second wall section 12b is filled with an expandable driving member or members, and the piston 29 is next added thereto in layered arrangement. Optionally, the piston 29 may be added to the first wall section 12a after filling the wall section with beneficial agent, in addition to, or instead of, the partition layer added to second wall section 12b, Next, the two sections at their open ends are slid together.

The delivery device can be manufactured for delivering numerous beneficial agents, including drugs, at a controlled rate to a presently preferred biological environment of use such as warm-blooded animals, including humans; ruminants, such as bovines and sheep; porcines, such as hogs and swine; horses; and the like. The delivery devices provide for high loading of a beneficial agent and for its improved delivery in beneficially effective amounts (that is, amounts that provide a beneficial effect) over time. It is to be understood that the delivery devices can take a wide variety of shapes, sizes and forms adapted for delivering beneficial agents to environments of use. For example, the devices manufactured as delivery devices can be used for dispensing a beneficial agent in the anal-rectal passageway, in the cervical canal, as an artificial gland, in the vagina, as a subcutaneous or intraperitoneal implant, and the like. The delivery devices can be used in hospitals, nursing homes, outpatient clinics, sickrooms, veterinary clinics, farms, zoos, and other environments of use.

EXAMPLE A1

A delivery device manufactured in the shape of an implantable delivery device is manufactured as follows.

An expandable driving member was prepared by first adding 10 liters of water and 526 g of polyvinylpyrrolidone to a stainless steel container and mixing the components for 1 hr to obtain a smooth binder solution. Next, approximately 20 kg of sodium chloride was milled in a mill to a number 21 size mesh screen. Then, 17.5 kg of the milled sodium chloride and 7.5 kg of sodium Carbomer®, a sodium salt of a polyacrylic polymer, were transferred to the granulator bowl of a fluid bed granulator and 2.46 kg of binder solution was slowly sprayed onto the materials in the granulator. Granules were formed in this manner. Next, the granulated material was sized by forcing it through a 0.0469 in mesh screen in a screen separator. Then, the granulation was divided into two 2.8 kg sub-batches. For each sub-batch, 130 g of magnesium stearate was added and the ingredients were blended for 3 min at 9 rpm to produce a homogeneous expandable driving composition. The composition next was pressed into osmotically active tablets in a tablet press at a pressure of 2,000 lbs to produce a round, flat-faced 266 mg tablet as an expandable driving member.

The semipermeable wall (membrane cup) that surrounds a compartment for containing the osmotically active tablets was prepared as follows. First, 1.0 kg of tributyl citrate and 9.0 kg of cellulose acetate butyrate were dry mixed in a mixer for 30 min. This produced a polymer/plasticizer blend of 90/10 ratio for the rate-controlling semi-permeable second wall section 12b. The blend was then injection molded into a semi-permeable membrane cup of the desired shape with an open end for receiving an expandable driving member and for mating with the forward wall section, whose preparation is as follows.

The impermeable first wall section 12a of the delivery device 10 which forms the compartment holding the beneficial agent 7, is prepared by blending the polypropylene (Himont PD626) with a blue colorant (0.1 FD & C blue lake). The mixture is then injection molded into the first or forward impermeable wall section 12a in the desired shape, with the open second end 34 for mating with the semi-permeable second wall section or membrane cup 12b and an open forward or lead end 32 for the end cap 38 That portion of the first wall section 12a which mates with the semi-permeable second wall section or membrane cup 12b is molded with a diamond shaped pattern over a portion of its surface to enhance the adhesive bond between it and the membrane cup. Surface preparation ensures satisfactory adhesive bonding of polypropylene to other materials. In the case of the first wall section 12a, in addition to the mechanical configuration described above, this may be accomplished by either applying a primer to the glue-joint area or by treating the surface with a plasma made from a mixture of oxygen and tetrafluromethane gases prior to applying the adhesive. That mating portion of the first or forward wall section which mates with the end cap 38 is molded with circumferential, rectangular-shaped mortise 102 to facilitate ultrasonically welding the end cap 38 to the forward wall section 12a as described more fully elsewhere in this application.

The end cap 38 was prepared by blending polypropylene (Himont PD626) with a blue or white colorant (0.1% FD & C blue lake or 1.0% titanium dioxide, respectively). This mixture is then injection molded to form the end cap 38, as described more fully earlier in this application, having the exit aperture with a 0.017 inch diameter approximately 0.1 inches long, an internal cavity for containing a wax sealant material, and a precisely determined circumferential configuration around the outer perimeter of the end cap 38 to facilitate ultrasonic welding of the cap to the forward wall section 12a. This configuration includes a wedge shaped energy director with an included angle of 56°, which is beneficial to achieving a high quality ultrasonic weld with crystalline, polymeric materials being joined. The internal cavity is filled with molten wax (Witco 145), which solidifies to form a seal to the orifice port.

The piston 29 is prepared by insert injection molding Monsanto brand thermoplastic elastomer sold under the brand name "Santoprene® 271-55", into the piston with a circumferential, cantilevered lip at each end and a metal detection core in its center. The metal core is cylindrical in shape with a flat face at each end and is manufactured in a separate process by sintering at 1300° F. a metal alloy consisting of nickel and iron in a 50/50 ratio. The metal core is inserted into the mold when it is in the open position, and the thermoplastic elastomer is injected around it during the injection molding process. The piston 29 thus formed is lubricated with silicone medical fluid to facilitate movement of the piston inside the device during assembly and operation and to minimize piston set during storage.

The delivery device 10 is partially assembled by first charging the second wall section or semi-permeable membrane cup 12b with six of the osmotic tablets 25a–f. The second wall section 12b is then partially inserted into the impermeable first or forward wall section 12a of the device 10 and two drops of moisture-cured cyanoacrylate adhesive are dropped onto the exposed portion of the joint between the first and second wall sections, where the adhesive is drawn into the remainder of the joint by capillary action. The first and second wall sections 12 and 12b are then fully inserted to form a mechanically strong, water-tight seal. The lubricated piston 29 is then inserted through the remaining open end 32 of the first or forward wall section 12a, using a tool which allows air to pass by the piston 29 as it is moved into position against the osmotic tablets 25a–f and insert the piston within the wall section without having the skirt member rolled. The tool used is a thin-walled funnel open at both ends having an internal chamber for receipt of the piston therein.

Next, the delivery device subassembly, comprised of the second wall section or membrane cup 12b, the osmotic tablets 25a–f, the impermeable first or forward wall section 12a and the piston 29, is filled with 2250 mg of the beneficial agent 7 formulation at 35° C. The formulation is comprised of 36.5%±1.5% for Zn-bST in a phosphate buffer, glycerols, wetting agent, salt excipient blend where the w/w/w/w proportions of phosphate buffer, glycerol, Tween-80, and KCl are 48.38/48.38/0.24/3.0 respectively. The phosphate buffer is 60:40 monobasic:dibasic sodium phosphate, and the molarity is 0.45. Then, a waxed end cap 38 is place into position on the open lead end 9 of the first wall section 12a by ultrasonic welding. The filled implant 10 is heat treated after being placed into a sterile package, for example, by heating the about 40° C. for about 16 hours.

EXAMPLE A2

The pistons of the configuration described in Example A1 were tested as follows:

A formulation of ZnbST in a phosphate/glycerol/Tween/NaCl excipient was prepared using titrated water ($^3H_2O$)). The specific activity of the labelled water was 1.0 mCi/ml, and should be sufficient to provide a detection limit of 1 mgm of water. The formulation was loaded into 10 mm osmotic implants with two different piston designs (1.0× and 1.5×), and a third group that had the compartment surrounding the osmotic driving member prehydrated.

TABLE 1

Pump configurations

| Group | Piston | Pre-hydration |
|---|---|---|
| 1 | 1.0x | no |
| 2 | 1.5x | no |
| 3 | 1.0x | yes |

The implants were sampled in duplicate for group 1, and triplicate for groups 2 and 3, at intervals of 0, 3, 6, 12 and 18 weeks. For measurement of total water transport to the osmotic driving members, e.g. salt tablets, of the internal chamber 18 surrounded by the semi-permeable wall section 12b, the second wall section 12b was separated from the first wall section 12a and the end cut off. Salt tablets were expelled and dissolved in water. An aliquot of the solution was added to the liquid scintilallation cocktail and counted by standard liquid scintillation counting techniques. Table 2 lists the individual measurements of the total water content.

TABLE 2

TRANSPORT OF WATER FROM THE FORMULATION COMPARTMENT TO THE ENGINE COMPARTMENT DURING STORAGE AT 4 C.

| Group/Replicate | Week 0 | Week 3 | Week 6 | Week 12 | Week 18 |
|---|---|---|---|---|---|
| 1/1 | 12 | 37 | 75 | 7413* | 130 |
| 1/2 | 12 | 50 | 68 | 98 | 148 |
| 1/3 | — | — | — | — | 162 |
| 2/1 | 460 | 43 | 66 | 331* | 515* |
| 2/2 | 14 | 41 | 67 | 97 | 150 |
| 2/3 | 1209* | 45 | 235* | 102 | 146 |
| 3/1 | 4 | 56 | 82 | 114 | 189 |
| 3/2 | 101* | 46 | 65 | 711* | 230* |
| 3/3 | 5 | 51 | 76 | 112 | 139 |

*Possible statistical outlier (greater than 3 standard deviations from mean excluding theses points).

Figure 23:
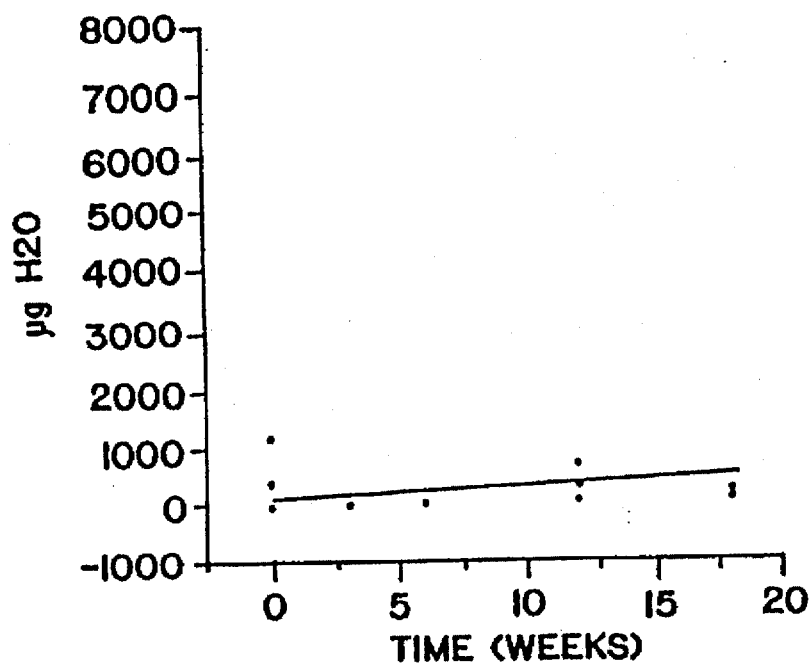
FIG. 23 is a graph showing passage of water by the piston of FIG. 18 from the internal compartment surrounded by an impermeable first wall section into the internal compartment surrounded by permeable second wall section of FIG. 16.

FIG. 23 is a graph depicting the relationship between mgms of $H_2O$ by-passing the piston versus time (weeks).

Figure 24:
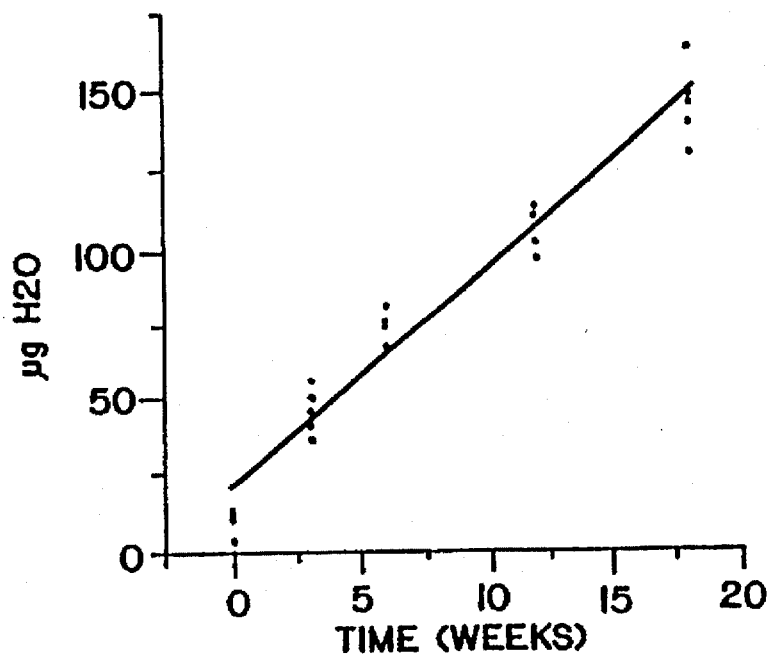
FIG. 24 is a graph showing passage of water by the piston of FIG. 18 from the internal compartment surrounded by an impermeable first wall section into the internal compartment surrounded by permeable second wall section of FIG. 16, excluding data ≧three standard deviations from the mean.

FIG. 24 is a graph showing mgms of $H_2O$ by-passing the piston versus time excluding outliers.

A variable amount of water (0.1–7 mg) transferred from the portion of the internal compartment 18 surrounded by the first wall section 12a to the portion surrounded by the second wall section 12b during the filling procedure for approximately 25% of the implants 10. There was a high pump to pump variability at all time points, on top of a small increase due to subsequent water transport from the internal compartment surrounded by the first wall section 12a to the salt tablets. The linear regression estimates of the rate of water transport along with 95% confidence intervals were as follows:

All data included: 20.0±8.9 mgms/week
excluding outliers: 7.1±0.1 mg/week

Thus, the worst case estimate (upper 95% confidence interval with all data included) was 28.9 mgms per week, or approximately 1.5 milligrams per year. The best case estimate (lower confidence interval excluding outliers) was 7.0 mgms per week, or 0.36 milligrams per year. Therefore it was concluded, assuming the acceptable limit set by the amount of water that can be lost from the formulation without exceeding a 1% increase in protein assay, is approximately 60 milligrams, that the piston tested in these experiments was deemed adequate to maintain separation between the portion the internal compartment 18 surrounded by the first wall section 12a and the portion of the internal compartment 18 surrounded by the semipermeable second wall section 12b for the anticipated shelf life of five years or more.

EXAMPLE A3

Delivery devices of the configuration as described in Example A1 were tested in vivo as follows.

Example A3a (11466)

Weekly Subcutaneously Administered Pellets

A study was undertaken to determine the effect of 40 or 80 mg A-bST pellets administered subcutaneously weekly during a 84-day beef cattle study on 1) growth, 2) feed efficiency and 3) carcass composition.

One hundred eighty Angus X Hereford beef steers weighing approximately 350 kg (770 lbs) were used. Stocking density was 5 animals per pen. The trial consisted of 180 steers with replicates of 12 pens (60 animals) per treatment group (control, 40 mg bST/wk, and 80 mg bST/wk). The study lasted 84 days (12 weeks) exclusive of the pretreatment period. The diet for all animals, on a dry matter basis, contained 16% crude protein ("P"). Potable water was available ad libitum. Pens were randomly distributed among treatments:

TABLE 3

| Trial | Group | Pens | Animals | Treatment Description |
|---|---|---|---|---|
| 1 | 1 | 12 | 60 | Control |
| 1 | 2 | 12 | 60 | 40 mg/wk A-bST Pellets |
| 1 | 3 | 12 | 60 | 80 mg/wk A-bST Pellets |

The animals were slaughtered for carcass analysis. The results are shown on the following Table:

TABLE 4

| Parameters | Control | 40 mg/wk bST Pellets | 80 mg/wk bST Pellets |
|---|---|---|---|
| Initial Body Wt (kg) | 390.3 | 390.3 | 390.3 |
| Final Body Wt (kg) | 499.5a | 495.0a | 510.4b |
| Carcass Wt. (kg) | 308.3 | 304.3 | 312.2 |
| Dressing Percent | 61.7 | 61.5 | 61.2 |
| Carcass Gain Response | — | No Gain | 39% |
| Non-Carcass Gain Response | — | No Gain | 61% | a, b - different superscripts indicate that numbers in a row are significantly different (p <.05)

It was observed that neither dressing percentage nor carcass weight were significantly increased. Further, at a higher dosage, most of the increase in body weight due to bST treatment was allocated to the non-carcass components.

Example A3b

Weekly Subcutaneous or Intraperitoneal Pellets

A study was undertaken to determine whether the effect of 80 mg A-bST pellets during an 84-day beef cattle study was comparable when administered subcutaneously and intraperitoneally.

Two hundred seventy Angus X Hereford beef steers weighing approximately 350 kg (770 lbs) were bought and divided into three study groups. Stocking density was 5 animals per pen. Each study group consisted of replicates of 6 pens (30 animals) per treatment group (control, 40 mgbST/wk subcutaneous pellet, and 80 mgbST/wk intraperitoneal pellet). The study lasted 84 days exclusive of the pretreatment period. The diet for all animals, on a dry matter basis, contained 16% crude protein. Potable water was available ad libitum. Pens were randomly distributed among the treatments:

TABLE 5

| Trial | Treatment | Pens | Animals | Description |
|---|---|---|---|---|
| 2 | 1 | 12 | 60 | Control |
| 2 | 2 | 12 | 60 | 80 mg/wk A-bST Subcutaneous (SQ) Pellet |
| 2 | 3 | 12 | 60 | 80 mg/wk A-bST Intraperitoneal (IP) Pellet |
| 3 | 1 | 12 | 60 | Control |
| 3 | 2 | 12 | 60 | 80 mg/wk bST SQ Pellet |
| 3 | 3 | 12 | 60 | 80 mg/wk bST IP Pellet |
| 4 | 1 | 12 | 60 | Control |
| 4 | 2 | 12 | 60 | 80 mg/wk A-bST SQ Pellet |
| 4 | 3 | 12 | 60 | 80 mg/wk A-bST IP Pellet |

The animals were slaughtered for carcass analysis. The results are shown in the following Tables:

TABLE 6

| | TREATMENT | | |
|---|---|---|---|
| Parameters | Control | 80 mg/wk SQ bST Pellets | 80 mg/wk IP bST Pellets |
| Carcass Wt. (kg) | 395.1 | 395.0 | 397.7 |
| Final Body Wt (kg) | 493.7a | 499.5a | 507.8a |
| Carcass Wt. (kg) | 304.2 | 304.2a | 311.2a |
| Dressing Percent (%) | 61.6a | 60.8b | 61.2ab |
| Carcass Gain (%) Response | — | 0% | 61% |
| Non-Carcass (%) Gain Response | — | 100% | 39% | a, b - different letters indicate that numbers in a row significantly different (p <.05)

It can be seen that, while the dressing percentage of subcutaneously-treated cattle was significantly decreased relative to the control, the dressing percentage of intraperitoneally-treated was not significantly changed relative to the control.

Example A3b

Combination of Intraperitoneal bST Osmotic Pump and Estrogen Pellets

A study was undertaken to determine whether the effects of intraperitoneal release of bST, of estrogen pellets, or of the combined effects of the two.

Two hundred fifty-six cross-bred large frame steers weighing approximately 430 kg (948 lb) were assigned to a control group and three treatment groups and implanted with intraperitoneal bST pumps or/and estrogen pellets. The bST formulation used was a 35% An bST load in a phosphate buffer, glycerol, Tween-80 and KCl excipient. The w/w/w % proportions respectively were 48.38/48.38/0.24/0%. The phosphate buffer was 60:40 monobasic:dibasic sodium phosphate at 1.0M. The time of release of both bST and estrogen was 87 days prior to slaughter. The results are shown in the following Table.

TABLE 7

| | TREATMENT | | | |
|---|---|---|---|---|
| Parameters | Control | 12 mg/d bST 0 Estrogen | 0 bST/ 200 ug/d Estrogen | 12 mg/d bST//200 ug/d Estrogen |
| Initial Body Wt (kg) | 430.3 | 430.3 | 430.3 | 430.3 |
| Final Body Wt (kg) | 544.9a | 552.2b | 567.1c | 576.4d |
| Carcass Wt (kg) | 334.2a | 340.3b | 349.3c | 359.7d |
| Parameters | Control | Estrogen | Estrogen | Estrogen |
| Dressing Percent (%) | 61.3a | 61.6a | 61.6a | 62.4b |
| Carcass Gain Response | N/A | 84% | 68% | 112% |
| Non Carcass Gain Response | N/A | 16% | 32% | −12% | a,b different superscripts indicate that number in a row are significantly different (P <.05) [what about c and d]

These results indicated that a significant improvement in dressing percentage and carcass weight were achieved by intraperitoneal osmotic pump release of bST concurrent with estrogen treatment.

Example A3c

Combination of Intraperitoneal bST Osmotic Pump and Estrogen Pellet

A study was undertaken to determine performance of intraperitoneal osmotic pumps in finishing cattle concurrently being administered estrogen. Six hundred seventy-two cross-bred large frame cattle weighing approximately 412 kg were bought and assigned to a control group and six treatment groups of 96 cattle each. The cattle were implanted with intraperitoneal osmotic pumps capable of delivering 6, 12, 15 or 18 mg bST per day during an 84-day period ending with slaughter. The cattle received estrogen pellets during a 126-day period ending with slaughter. The estrogen release is estimated at about 200 μg/d. The results are shown in the following table.

TABLE 8

| | | TREATMENT | | | | | |
|---|---|---|---|---|---|---|---|
| load | | 30% | | 40% | | 45% | |
| Parameters | Control | 6 µg/d | 12 µg/d | 6 µg/d | 12 µg/d | 12 µg/d | 18µg/d |
| Initial Body Wt (kg) | 411.9 | 411.9 | 411.9 | 411.9 | 411.9 | 411.9 | 411.9 |
| Final Body Wt (kg) | 555.1a | 565.6bc | 568.7bc | 569.6c | 561.8b | 563.5bc | 566.5bc |
| Carcass Wt (kg) | 343.0a | 353.1bc | 357.2d | 355.4cd | 350.8b | 351.3b | 53.8bcd |
| Dressing Percent | 61.8a | 62.4b | 62.8b | 62.4b | 62.4b | 62.4b | 62.5b |
| Carcass Response | — | 96% | 104% | 86% | 116% | 99% | 95% |
| Non-Carcass Response | — | 4% | –9% | 14% | –16% | 1% | 5% |

The results confirm that concurrent intraperitoneal treatment of finishing beef cattle with bST and estradiol significantly increase dressing percentage and carcass weight and furthermore allocated most of the increased weight to the carcass components.

EXAMPLE A4

Figure 25:
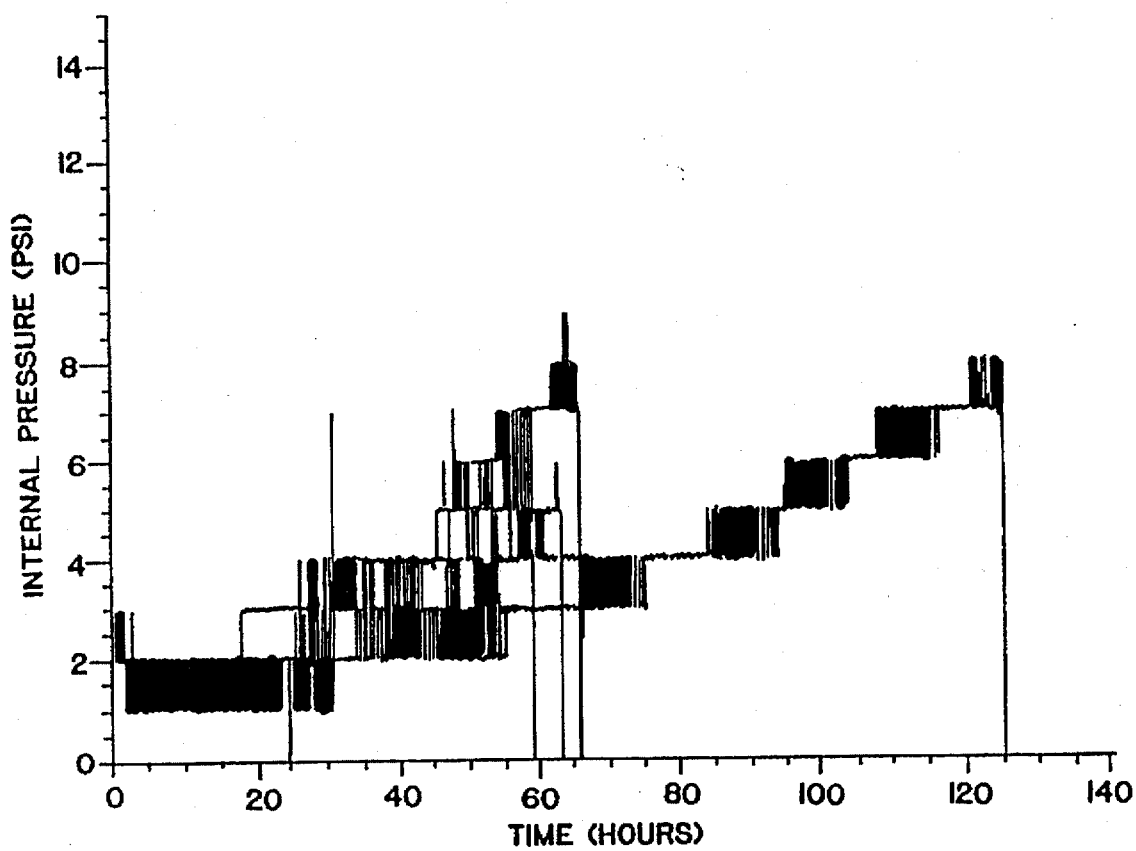
FIG. 25 is a graph depicting the real time pressure release for a seal of Multiwax X-145a wax having a thickness of 0.050 inches.

FIG. 25 is a graph depicting the real time pressure release for a seal of Multiwax X-145a wax having a thickness of 0.050 inches. The pressure at which the seals blew was between 6 and 9 psi from exit passageway of having a 0.017 diameter and a length of 0.100 inches.

Thus, an exit passage having a 0.017 inch diameter and a length of 0.100 inches, in fluid contact or abutted by a seal of 0.050 thick, would burst the seal between about 6–9 psi.

EXAMPLE A5

Figure 26:
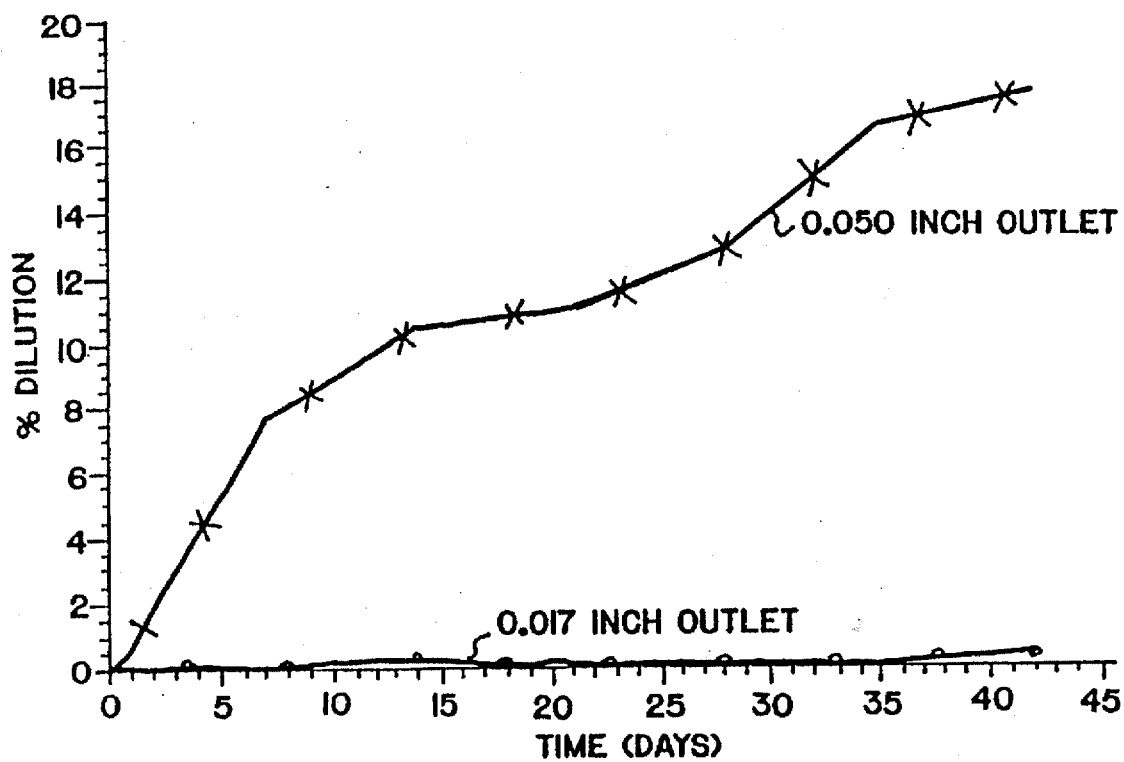
FIG. 26 is a graph showing the effect of the exit port aperture diameter on the diffusion of water using an exit passageway length of 0.100 inches and specified diameter.

FIG. 26 is a graph showing the effect of the exit port aperture diameter on the diffusion of water using an exit passageway length of 0.100 inches and specified diameter. Empirical observations of the respective devices indicate that the beneficial agent formulation turned white in all devices with 0.050 inch diameter outlets with small pockets of water entrained in the formulation. The beneficial agent formulation was clear in all devices having an exit port aperture of about 0.017 inches in diameter.

Thus an exit aperture having a diameter of 0.017 inches provides sufficient outward velocity or efflux of the beneficial agent from the compartment defined by the first wall section, i.e., "substantially limits or prevents" diffusion of fluid back into the internal compartment defined by the first wall section under these conditions of use obviously the diameters and lengths of the aperture needed to effect the desired flow rate will vary with the optimum conditions of delivery/usage of the particular beneficial agent.

The devices use means for the obtainment of precise release rates in a fluid environment of use while simultaneously maintaining the integrity of the device and the stability of the fluid-sensitive beneficial agent 7 within the device.

SUPPLEMENTAL EXEMPLARY EMBODIMENT B

Methods For Use of the Invention

The invention may be used in a method of preparing beef cattle in the finishing stage of growth for slaughter. The finishing stage of growth is the final stage of growth before slaughter, and follows the stocker stage of growth when the bovine receives nutrients primarily from pasturage or hay, optionally with feed supplementation, which in turn follows the calf or suckling stage when the calf receives nutrients primarily from its mother.

Cattle in the finishing stage of growth are generally nonlactating bovines (steers or heifers) of 12 months (or even as low as 3 months) to 2 years of age who are undergoing rapid growth. The finishing stage of growth can be regarded as beginning when the typical beef stocker is about 700 pounds (about 320 kg) of weight. Such animals will usually be slaughtered when a weight of about 1000 or 1300 pounds (about 450 kg or 600 kg) or more is reached.

The finishing stage of growth is a period of time during growth when the bovine is of sufficient size and age when supplied with a suitable feed to undergo a rapid average daily weight gain, for example, an average daily gain of at least 1 kg/d, that is, when the rate of weight gain is 1 or more than 1 kg/d. Typically, cattle during this phase of growth can gain in the range of about 1 to about 2 kilograms or even more per day. Preferably, the cattle are high-performance cattle capable of growth at a rate of greater than about 1.5 kg/d, most preferably at a rate greater than about 1.7 kg/d. The current limit of average daily gain (ADG) during finishing is about 3 kg/d; however, as higher performance cattle are developed, this limit may be exceeded. In any case, the range above 1 or 1.5 etc. kg/d is finite and definite and will be known to those skilled in the art.

During the finishing stage of growth, the bovine feed may be supplemented with concentrated feed, richer than pasturage or hay in digestible proteins, carbohydrates, and fats. Typically, during the finishing stages, feed grain may constitute from 12 to 80% or more of the animal's feed. The feed may contain from 12 to 16 percent or more protein or protein-equivalent nitrogen. National Research Council. (NRC) guidelines permit finishing at as low as 9% protein-equivalent nitrogen.

It has been found that feed efficiency, body and carcass weight and dressing percent are advantageously influenced when beef cattle receiving an estrogenic agent are treated intraperitoneally with an effective dose and rate of release of bST during this period of growth.

bST (bovine somatotropin) refers to any protein having bovine somatotropin activity. The bovine somatotropin can be pituitary-derived or recombinantly produced bovine somatotropin. The bST can be a naturally-occurring sequence or a sequence altered by addition or deletion or substitution of one or more amino acids. All of these forms of bovine somatotropin are now well-known to those skilled in the art.

Examples of bovine somatotropin variants include, but are not limited to, polypeptides having the following amino acid sequences with unspecified amino acid residues being the same as or similar to the naturally occurring somatotropin:

$NH_2$-met-phe(1)-pro(2) . . . leu(126) . . . phe(190)-COOH $NH_2$-met-phe(1)-pro(2) . . . val(126) . . . phe(190)-COOH $NH_2$-ala-phe(1)-pro(2) . . . val(126) . . . phe(190)-COOH $NH_2$-ala-phe(1)-pro(2) . . . leu(126) . . . phe(190)-COOH $NH_2$-phe(1)-pro(2) . . . leu(126) . . . phe(190)-COOH $NH_2$-phe(1)-pro(2) . . . val(126) . . . phe(190)-COOH $NH_2$-met-asp-glu-phe(1)-pro(2) . . . leu(126) . . . phe(190)-COOH $NH_2$-met-asp-glu-phe(1)-pro(2) . . . val(126) . . . phe(190)-COOH $NH_2$-met(4)-ser(5) . . . leu(126) . . . phe 190)-COOH $NH_2$-met(4)-ser(5) . . . val(126) . . . phe(190)-COOH $NH_2$-met-phe(10) . . . leu(126) . . . phe(190)-COOH $NH_2$-met-phe(10) . . . val(126) . . . phe(190)-COOH The first variant in the list above, with a methionyl residue at the N-terminus, and a leucyl residue at position 126 may be specifically referred to as methionyl bovine somatotropin or "MBS", and the third variant in the list above, with an alanyl residue at the N-terminus and a valyl residue at position 126 may be referred to as alanyl-valyl bovine somatotropin or "ala-val BST" or "A-BST". Metal complexes of such bST, such as zinc and copper complexes, may also be used and are referred to as Zn-bST or Cu-bST. See, e.g., U.S. Pat. No. 4,863,736.

It is understood that the additional N-terminal methionyl residue on the variants described above could also be removed, either during or after expression. It is also understood that one or more amino acids of the following sequence -glu-arg-ala-tyr-ile-pro-glu- (which are numbers 32-38 of the bovine somatotropin sequence set forth above) may be deleted. This type of deletion is described in European Patent Application, Publication Numbers 282,318, and 282,319, both of which were published Sep. 14, 1988. Other deletion variants with somatotropin activity can also be used, such as deletion of amino acids 32-45.

The somatotropins found most effective for administration are those which have an N-terminal group of methionine and are associated with zinc metal. See, e.g., U.S. Pat. No. B1 4,985,404, incorporated herein by reference.

The formulation of bovine somatotropin for use in an osmotic implant may generally include a stabilizing polyol. The phrase "stabilizing polyol" means polyol, for example, with three hydroxyl groups, which maintains the somatotropin in a physically stable composition, i.e. the somatotropin does not precipitate to an undesirable degree over reasonable storage or administration period. Glycerol is the preferred polyol, however, other polyols may be used, such as tris (hydroxymethyl)aminomethane.

The formulation may further include a physiologically compatible buffer, incorporated for maintaining the pH exhibited by the composition within a range in which the somatotropin is bioactive. Generally, the pH exhibited by the solution should be between a minimum of about 4.5 or, preferably about 5, or more preferably 5.7 and a maximum of the greater of about 7 and about the isoelectric point of the somatotropin. The isoelectric point for A-BST is 8.6. These isoelectric points are for the standard monomeric forms obtained in bulk preparation of these somatotropins. Isoelectric points for other variants, other derivatives and other forms can be determined using standard techniques. For A-BST, the optimum pH is about between about 6.1 and about 7.5. Although various buffers can be used, it is preferred that the buffer be an alkali metal phosphate. To provide buffering in the desired pH range, it is particularly preferable that the buffer be comprised substantially of monobasic:dibasic phosphates such as, for example, mono- or-di-sodium or potassium phosphates at 1M or 0.45M or the like. Another effective buffer for controlling the pH in the desired range is a histidine hydrohalide such as histidine hydrochloride. Additional buffers that maintain this pH range are citrate buffers and acid addition salts of tris (hydroxymethyl)aminomethane, such as the hydrochloride salt. These tris(hydroxymethyl)aminomethane salts also contain hydroxyl groups and can act as a stabilizing polyol in some circumstances. Any other buffer that can maintain a pH in the desired range can be used.

It should incidentally be noted that direct measurement of the pH of the composition may not in all instances be practical. To provide a practical measurement, however, a small quantity such as a drop of the composition may be placed in about 10 ml of water, and the pH of the resulting mixture determined. It is believed that the actual pH of the composition is closely approximated by this measurement, but, in any event, it will be understood that the pH measured at such dilution is considered for purposes of this disclosure to be the pH exhibited by the composition itself.

In order to promote wetting of the somatotropin by the buffer/polyol excipient during preparation of the formulation, a wetting agent, such as a nonionic surfactant is preferably incorporated as well. Such surfactant also inhibits foaming. The surfactant can be present in the excipient at amounts between about 0.005% and about 2.5% more preferably about 0.25%. A particularly preferred nonionic surfactant is a polyethoxylated sorbitan ester, such as a tri(polyoxyethylene) ester of sorbitan mono-oleate, such as that sold under the trade designation Tween 80 by ICI Americas Inc.

An advantage of the use of a buffered polyol excipient for the somatotropin is the high loading achievable due to the high solubility of the somatotropin in the excipient liquid. Despite the high concentration of somatotropin in a composition which also contains a significant fraction of water, the pH maintained by the buffer inhibits the formation of dimers and other aggregates. Although it has not been determined whether the somatotropin is true solution or colloidal solution, it is desirable that the somatotropin does not precipitate or otherwise separate from the excipient, either on standing or under the influence of shear encountered in passage of the composition through the discharge opening of an infusion pump. The concentration of somatotropin in the composition is at least about 10% by weight, preferably at least about 15% by weight, more preferably at least about 20% by weight and even more preferably at least about 25% or even about 30% by weight. The somatotropin concentration may range as high as about 45% by weight.

The polyol concentration may be at least about 20% by weight or 25% by weight and may range as high as 80% by weight or 70% by weight or 60% by weight or 50% by weight or 40% by weight. A relatively high glycerol content additionally provides a bacteriostatic effect. It is generally considered that an excipient containing about 50% glycerol provides bacteriostatic effect. The osmotic implant may further contain an estrogenic agent, for example, 17-estradiol, at a concentration of about 0.005 to about 1%, more preferably about 0.18 to about 0.72%.

Preferably, the formulation further comprises a wetting agent, such as nonionic surfactant with optimum concentrations between about 0.005% or about 2.5% by weight. Except for the buffer salt, which in the case of a phosphate buffer may typically comprise 4% to 7% by weight, and the sodium or potassium chloride which may be added to stabilize the formulation, described below, the balance of the formulation typically is water. A preferred formulation contains at least about 7% water, more preferably at least about 15% water, and even more preferably between about 25% and about 35% by weight water.

Optionally an alkaline halide such as sodium chloride or potassium chloride is added to the excipient prior to formulation with somatotropin. It has been found that this facilitates maintaining homogeneity of the formulation during filling of the implants, for example, when using Zn-bST. Following addition of the somatotropin to the excipient, the filled implant can be subjected to heat treatments from about 6 to 24 hours, preferably 16 hours, at a temperature between about 35° C. and 50° C., preferably 39°–46° C., most preferably about 40° C. Preferably the alkaline chloride comprises about 1 to about 4% by weight of the final formulation.

The formulation is normally a clear, homogeneous single phase. The formulation appears as a solid or semisolid at typical storage temperatures of about 4° C. The formulation decreases in viscosity to produce a viscous liquid at the body temperature of an animal. In this way, the formulation can be dispensable without being readily fluid at all temperatures.

As the concentration of somatotropin rises above 25%, the ratios of water and buffer to somatotropin preferably decline with increasing somatotropin concentration so as to maintain a polyol concentration as high as practicable. However, polyol content is limited by viscosity considerations, and the maximum polyol concentration is about 40–45% for formulations having a hormone content about 25%. Higher polyol concentrations provide a benefit in physical stability, but can result in viscosity that makes handling difficult.

Preferably the bST is an aqueous suspension of bST formulated for release in an osmotic pump as hereinafter described. Such formulations can include glycerol, monobasic and dibasic sodium phosphate buffer, Tween-80, an alkaline halide salt such as sodium chloride and/or potassium chloride, but are not limited to these ingredients, in addition to the active ingredients such as bST and the estrogenic agent.

The currently preferred formulation comprises 36.5% 1.5% for Zn-bST in a phosphate buffer, glycerols, wetting agent, salt excipient blend where the w/w/w/w proportions of phosphate buffer, glycerol, Tween-80, and KCl are 48.38/48.38/0.24/3.0 respectively. The phosphate buffer is 60:40 monobasic:dibasic sodium phosphate, and the molarity is 0.45.

The preferred composition containing an estrogenic agent comprises about 0.06% to about 3.0% 17-beta-estradiol.

bST is intraperitoneally released in beef cattle in the finishing stages of growth at an effective dose and rate for significantly increasing a parameter selected from the group consisting of: body weight (BW), carcass weight (CW), average daily gain (ADG) or feed efficiency (FE) of the animal. By significantly increasing is preferably meant that the dose is preferably effective at $P<0.05$ which is a standard for demonstrating a beneficial effect.

The peritoneum is the serous membrane lining of the abdominal walls (parietal peritoneum) and investing the viscera (visceral peritoneum). The parietal peritoneum is the membrane which lines the abdominal and pelvic walls and the undersurface of the diaphragm. The visceral peritoneum is the membrane reflected at various places over the viscera, forming a complete covering for the stomach, spleen, liver, ascending portion of the duodenum, jejunum, ileum, transverse colon, sigmoid flexure, upper end of the rectum, uterus, and ovaries; it also partially covers the descending and transverse portions of the duodenum, the cecum, ascending and descending colon, the middle part of the rectum, the posterior wall of the bladder, and the upper portion of the vagina. The peritoneum serves to hold the viscera in position by folds, some of which form the mesenteries, which connect portions of the intestine with the posterior abdominal wall; others, the omenta, folds attached to the stomach, and still others, the ligaments of the liver, spleen, stomach, kidneys, bladder, and uterus. The space between the parietal and visceral peritoneums is the Peritoneal Cavity, which consists of the Pelvic Peritoneal Cavity below and General Peritoneal Cavity above. The General Peritoneal Cavity communicates by the Foramen of Winslow with the Cavity of the Great Omentum, which is also known as the Lesser Peritoneal Cavity. As used herein, intraperitoneal cavity includes any of the Pelvic Peritoneal Cavity, the General Peritoneal Cavity, and the Lesser Peritoneal Cavity. More preferably, the implant is inserted into the Lesser Peritoneal Cavity.

It has been established that access to the peritoneal cavity is best gained by inserting a trocar through the left paralumbar fossa. Initially, it was thought that insertion through the right paralumbar fossa would be the preferred side, as the rumen is positioned adjacent to the left paralumbar fossa. However, it was determined that the position of the kidneys and associated kidney are asymmetrically distributed toward the right side of the body and interfere with trocar access to the peritoneal cavity. For this reason access to the peritoneal cavity is more easily accomplished through the left paralumbar fossa.

The implantation is preferably accomplished using a two step procedure. In the first step, a vertical incision is made substantially through the hide alone of the left paralumbar fossa. The incision is vertical relative to the ground and preferably less than 25 mm or 20 mm in length. In the second step, a sterile non-toxic plastic tube having, for example, a 30 bevel at the tip, optionally double-beveled, and providing a substantially-non-incising puncturing tip, is inserted through the incision and into the peritoneum. Sterile implants are inserted therethrough and the tube is removed and the wound permitted to close.

The bST is intraperitoneally released since it has been observed that subcutaneous daily injections or prolonged non-intraperitoneal release can result in a decrease or in a nonsignificant change in dressing percentage and have not resulted in significant increases in dressing percentage and carcass weight.

Generally, it has been found that a practical minimum rate of release for observing significant changes in body weight or carcass weight or average daily gain or feed efficiency is about 3 mg/d bST and that above about 14 mg/d bST, there is little additional improvement. For advantageous results, the intraperitoneal daily release is maintained preferably in the range of about 3 mg/d to about 14 mg/d. However, higher dosages can also be employed. More preferably the intraperitoneal daily release is maintained in the range of about 6 or 9 to about 12 mg/d.

The release is preferably continuous since daily injections or biweekly injections can cause a reduction in dressing percentage. See, e.g., Mosley et al., op. cit., and Wright et al., op. cit. However, a pulsatile intraperitoneal release enhancing dressing percent is suitable, for example, a pulsatile release 6, 12 or more times per day so that noncarcass growth is not unduly stimulated.

The preferably continuous release can be zero-order or non-zero order provided that the release threshold is preferably maintained in the range of above about 3 mg/d to about 14 mg/d, more preferably in the range of about 9 to about 12 mg/day that is, provided that the rate of release does not fall below a value in these ranges during substantially the entire period of treatment. Preferably, also, the rate of release does not exceed values of these ranges since higher dosages of bST which are not maintained over the long term may favor increase in weight of non-carcass organs and such higher dosages may result if a prolonged continuous intraperitoneal release above the minimum is to be achieved using a non-zero release implant.

bST is released at a substantially zero-order rate of release when the rate of release is substantially independent of the amount of bST remaining in the implant. It is preferred that the release be substantially zero-order. Thus, for example, a constant rate of release is zero-order. Such a rate of release can be accomplished by an osmotic implant such as described in Supplemental Exemplary Embodiment A.

Preferably the bST administration is effected by such an implantable device capable of delivering the desired dose of bST intraperitoneally for a prolonged period of time. Preferably, as indicated, the osmotic implant is such as is described in Supplemental Exemplary Embodiment A. Other methods of achieving a substantially zero-order rate of release can also be used, for example, a pellet of bST having an approximately constant-area release surface, or using other techniques known to those skilled in the art.

In the prior art, bST daily injection produced serum bST levels that were 400 to 700% higher than baseline for the first four hours post-injection and returned to baseline about 12 hours after injection (Enright et al., 1990 and Early et al., 1990a); whereas continuous bST delivery from a pellet has been found to produce about a 100% increase in serum bST in Holstein heifers and no detectable increase in serum bST in cross-bred steers. These data support a hypothesis, which should not be considered to limit the invention, that a less-variable more-continuous rate of delivery of bST in steers may reduce the disproportionate growth of non-carcass components by establishing an effective blood level for promoting growth of the carcass components that does not exaggerate the growth of viscera and other non-carcass components. Wagner et al., 1988, for example, used continuous delivery of bST in an oil based system at a dose of about 70 mg/d and showed a significant reduction in dressing percent. This might indicate that viscera and other non-carcass components have a broader bST dose-response window than components of the carcass. Concomitantly, the dose used by Wagner et al., 1988 was far in excess of that described as preferred herein. In a companion study Wagner et al., 1988, showed that a 960 mg dose administered about every two weeks produced about a 38-fold (3770% increase) in serum bST levels, when examined twelve days post injection of the second 960 mg dose. Such blood level changes in bST are in far excess of those required to stimulate carcass growth in steers, but potentially within the dose response of tissues associated with the non-carcass component. Accordingly, a controlled release of bST within the window for increasing dressing percentage is preferred.

In Example B4 below, intraperitoneal bST osmotic implants in feedlot cattle increased dressing percent from 61.8% for the controls up to 62.4 to 62.8% for bST treated animals. Possible explanations for this effect included 1) presence of performance enhancers (e.g., an estrogenic agent) and 2) the mode of delivery (zero-order intraperitoneal delivery). In Example B3 below, the synergistic effect of an estrogenic agent and intraperitoneal zero-order delivery of bST is demonstrated. Neither product alone caused a significant increase in dressing percent, but in combination-treated cattle there was a significant increase in dressing percent.

In a study in which cattle received an estrogenic agent and intraperitoneal bST pellets, dressing percent was not significantly affected by treatment. However, as noted above, Wagner et al., 1988 had tested a combination of an estrogenic agent and bST delivered on a continuous basis, but had found that dressing percent still dropped from 63.0% to 61.4%. It is possible that Wagner et al.'s failure to demonstrate a bST/estrogen-induced improvement in dressing percent was due to 1) the excessive bST dose (70 mg/d) and/or 2) poorly controlled bST delivery (a 960 mg 28-day dairy product injected every 14 days). Thus, the enhancement of dressing percent with an estrogenic agent and intraperitoneal bST zero-order delivery can be considered due to factors including, 1) the synergistic effects of bST and the estrogenic agent, 2) the effect of substantially zero-order osmotic bST delivery and 3) the effect of intraperitoneal delivery compared to subcutaneous delivery of bST.

Most preferably, the implant is such as described in Supplemental Exemplary Embodiment A attached hereto and incorporated by reference. Such implants may contain about 800 mg bST and release bST at a nominal rate of about 6 to 7 mg/d. Two or more implants can be used concurrently to achieve a desired rate of release, for example, about 10 mg/d to 12 mg/d.

The implant, preferably providing a substantially constant release, is implanted in the intraperitoneal cavity of the bovine being treated. Implanting in the intraperitoneal cavity facilitates recovery of the implant with the non-carcass components of the bovine following slaughter. In addition, the combination of intraperitoneal implant and substantially constant release has been found advantageous in facilitating a significant increase in dressing percent and carcass weight in bST-treated cattle.

Implantation is preferably accomplished via the left paralumbar fossa since this has been found, as indicated above, to facilitate implantation. The left paralumbar fossa is a generally triangular area on the bovine between the hip bone and the last rib and below the loin area on the left side. Tissue and hide depth here is about 0.5 to 2.0", but trocars used for implantation are generally on the order of 1 to 5 inches. The insertion depth of the trocar needs to be greater than the actual thickness of the paralumbar region due to stretching of the peritoneal lining. The only internal organs presenting a risk of injury is the rumen. Damage to the rumen can be eliminated or reduced by administering the implant to fasting or feed restricted animals. Other methods of intraperitoneal administration may also be used.

bST is released intraperitoneally concurrently with administration of an effective dose of an estrogenic agent.

The estrogenic agent can be administered either subcutaneously or intraperitoneally.

Any estrogenic substance may be used as the estrogenic agent. An estrogenic substance is one which when administered to a normal female animal will cause growth of the uterus and teats. However, only estrogenic substances which are suitable for administration to food animals can be put into actual use.

In actual use, the acceptable estrogens for food-producing animals are estrone and estradiol steroids such as 17-beta estradiol, estradiol benzoate, ethinylestradiol, etc. or non-steroidal compounds with estrogenic activity, such as diethylstilbesterol, hexestrol, dianestrol, zeranol, etc., and derivatives of these substances. The simple esters, such as the C1–C6 alkanoates, and the benzoates, formed on one or two of the available hydroxy groups of estradiol and zeranol, or on the one hydroxy group of estrone are useful estrogenic substances. For example, estradiol benzoate, estradiol dipropionate, estrone acetate, zeranol hexanoate, zeranol dibutyrate, 17-beta-estradiol, 17-beta-ethinyl-estradiol, can be used.

Other components which do not interfere with the desired estrogen effect, such as progesterone, cholesterol, and other binding agents, and additives may also be present.

Broadly the estrogen can be released in the range of about 5 ug/d to 500 ug/d or even higher. Preferably the estrogen is released in the range of about 15 to about 60 ug/d. Generally, the dose of estrogenic agent can advantageously be the same as that used when the estrogenic agent is administered as an anabolic agent to cattle in the finishing stage of growth to significantly increase body weight (BW) or carcass weight (CW). When the estrogenic agent is released from an intraperitoneal osmotic pump, the effective dose may be even lower, for example, in the range of 15 to 30 ug/d.

As indicated, the estrogenic agent is delivered concurrently with the intraperitoneal release of bST, The administration of the estrogenic agent can be by pellets or other means such as are well-known in the art. Preferably, the estrogenic agent is delivered intraperitoneally in the bovine using an osmotic pump, for example, the osmotic pump employed for the bST or another separate osmotic pump containing the estrogenic agent in a suitable excipient.

Preferably, the estrogenic agent is released in the bovine for a period of time generally concurrent with the period of bST delivery. However, treatment with an estrogenic agent prior to and concurrent with initial bST treatment has also been found effective.

Preferably the bST and/or estrogenic agent implant is implanted into the animals at the beginning of the finishing stage of growth. However, either the estrogenic source or the bST implant or both may also be implanted earlier and either provide a delayed initiation of bST release or a longer period of release.

The intraperitoneal bST release is provided preferably during the entire period of the finishing stage of growth and is continued substantially until the time for slaughter of the animals. It has been previously found that the benefits of bST treatment may be adversely affected by discontinuation of bST. Hence, it is preferred that bST treatments continue at least until a time when the beneficial effects of concurrent bST and estrogen treatment will persist at slaughter, for example, until about two weeks before slaughter and most preferably that bST release be ongoing at slaughter.

The period of time during which an effective rate of intraperitoneal release must be maintained can be any period effective for significantly increasing dressing percentage and carcass weight in finishing cattle receiving an estrogenic agent. Currently, it is believed that a minimum of about 6 or even about 9–12 weeks are required. The period of bST release is preferably at least for about 12 weeks prior to slaughter and more preferably about 18 or more weeks prior to slaughter. Overall, the period of bST treatment can be from about 6 to about 24 or 30 weeks or longer preceding slaughter of the beef cattle.

To obtain full benefit of the intraperitoneal release of bST, it is preferred that the bovines be on a supplemented diet, that is, on a diet that contains more protein or carbohydrate or fat or combinations of these than is found in hay or pasturage.

EXAMPLE B1

Weekly Subcutaneously Administered Pellets

A study was undertaken to determine the effect of 40 or 80 mg A-bST pellets administered subcutaneously weekly during a 84-day beef cattle study on 1) growth, 2) feed efficiency and 3) carcass composition.

One hundred eighty Angus X Hereford beef steers weighing approximately 350 kg (770 lbs) were used. Stocking density was 5 animals per pen. The trial consisted of 180 steers with replicates of 12 pens (60 animals) per treatment group (control, 40 mg bST/wk, and 80 mg bST/wk). The study lasted 84 days (12 weeks) exclusive of the pretreatment period. The diet for all animals, on a dry matter basis, contained 16% crude protein ("P"). Potable water was available ad libitum. Pens were randomly distributed among treatments:

| Trial | Treatment Group | Pens | Animals | Description |
|---|---|---|---|---|
| 1 | 1 | 12 | 60 | Control |
| 1 | 2 | 12 | 60 | 40 mg/wk A-bST Pellets |
| 1 | 3 | 12 | 60 | 80 mg/wk A-bST Pellets |

The animals were slaughtered for carcass analysis. The results are shown on the following Table:

TABLE

| Parameters | Control | 40 mg/wk bST Pellets | 80 mg/wk bST Pellets |
|---|---|---|---|
| Initial Body Wt (kg) | 390.3 | 390.3 | 390.3 |
| Final Body Wt (kg) | 499.5$^a$ | 495.0$^a$ | 510.4$^b$ |
| Carcass Wt. (kg) | 308.3 | 304.3 | 312.2 |
| Dressing Percent (%) | 61.7 | 61.5 | 61.2 |
| Carcass Gain Response %) | — | No Gain | 39% |
| Non-Carcass Gain Response (%) | — | No Gain | 61% |

$^{a,b}$different superscripts indicate that numbers in a row are significantly different (p <.05).

It was observed that neither dressing percentage nor carcass weight were significantly increased. Further, at the higher dosage, it was observed that most of the increase in body weight due to bST treatment was allocated to the non-carcass components.

EXAMPLE B2

Weekly Subcutaneous Intraperitoneal Pellets

A study was undertaken to determine whether the effect of 80 mg A-bST pellets during an 84-day beef cattle study was comparable when administered subcutaneously and intraperitoneally.

Two hundred seventy Angus X Hereford beef steers weighing approximately 350 kg (770 lbs) were bought and divided into three study groups. Stocking density was 5 animals per pen. Each study group consisted of replicates of 6 pens (30 animals) per treatment group (control, 40 mgbST/ wk subcutaneous pellet, and 80 mgbST/wk intraperitoneal pellet). The study lasted 84 days exclusive of the pretreatment period. The diet for all animals, on a dry matter basis, contained 16% crude protein. Potable water was available ad libitum. Pens were randomly distributed among the treatments:

| Trial | Treatment | Pens | Animals | Description |
|---|---|---|---|---|
| 2 | 1 | 12 | 30 | Control |
| 2 | 2 | 12 | 30 | 80 mg/wk A-bST Subcutaneous (SQ) Pellet |
| 2 | 3 | 12 | 30 | 80 mg/wk A-bST (IP) Intraperitoneal Pellet |
| 3 | 1 | 12 | 30 | Control |
| 3 | 2 | 12 | 30 | 80 mg/wk bST SQ Pellet |
| 3 | 3 | 12 | 30 | 80 mg/wk bST IP Pellet |
| 4 | 1 | 12 | 30 | Control |
| 4 | 2 | 12 | 30 | 80 mg/wk A-bST SQ Pellet |
| 4 | 3 | 12 | 30 | 80 mg/wk A-bST IP Pellet |

The animals were slaughtered for carcass analysis. The results are shown in the following Tables:

TABLE

| | TREATMENT | | |
|---|---|---|---|
| Parameters | Control | 80 mg/wk SQbST Pellets | 80 mg/wk IPbST Pellets |
| Initial Body Wt (kg) | 395.1 | 395.0 | 397.7 |
| Final Body Wt (kg) | 493.7$^a$ | 499.5$^a$ | 507.8$^b$ |
| Carcass Wt. (kg) | 304.2$^a$ | 304.2$^a$ | 311.2$^b$ |
| Dressing Percent (%) | 61.6$^a$ | 60.8$^b$ | 61.2$^{ab}$ |
| Carcass Gain Response (%) | — | 0% | 61% |
| Non-Carcass Gain Response (%) | — | 100% | 39% |

$^{a,b}$different superscripts indicate that numbers in a row are significantly different (p <.05).

It can be seen that, while the dressing percentage of subcutaneously-treated cattle was significantly decreased relative to the control, the dressing percentage of intraperitoneally-treated cattle was not significantly changed relative to the control.

EXAMPLE B3

Combination of Intraperitoneal bST Osmotic Pump and Estrogen Pellets

A study was undertaken to determine the effects of intraperitoneal release of bST, of subcutaneous estrogen pellets, or of the combined effects of the two.

Two hundred fifty-six cross-bred large frame steers weighing approximately 430 kg (966 lb) were assigned to a control group and three treatment groups and implanted with intraperitoneal bST pumps or/and subcutaneous estrogen pellets. The bST formulation used was a 35% Zn$^-$ bST load in a phosphate buffer, glycerol, and Tween-80. The w/w/w% proportions respectively were 48.38/48.38/0.24. The phosphate buffer was 60:40 monobasic:dibasic sodium phosphate at 1.0M. The time of release of both bST and estrogen was 87 days prior to slaughter. The results are shown in the following Table.

TABLE

| | TREATMENT | | | |
|---|---|---|---|---|
| Parameters | Control | 12 mg/d bST 0 Estrogen | 0 bST/ 200 ug/d Estrogen | 12 mg/d bST// 200 ug/d Estrogen |
| Initial Body Wt (kg) | 430.3 | 430.3 | 430.3 | 430.3 |
| Final Body Wt (kg) | 544.9$^a$ | 552.2$^a$ | 567.1$^b$ | 576.4$^d$ |
| Carcass Wt (kg) | 334.2$^a$ | 340.3$^b$ | 349.3$^c$ | 359.7$^d$ |
| Dressing Percent (%) | 61.3$^a$ | 61.6$^a$ | 61.6$^a$ | 62.4$^b$ |
| Carcass Gain Response (%) | N/A | 84% | 68% | 112% |
| Non-Carcass Gain Response (%) | N/A | 16% | 32% | −12% |

$^{a,b}$different superscripts indicate that number in a row are significantly different (P >.05)

These results indicated that a significant improvement in dressing percentage and carcass weight were achieved by intraperitoneal osmotic pump release of bST concurrent with estrogen treatment.

EXAMPLE B4

Combination of Intraperitoneal bST Osmotic Pump and Estrogen Pellet

A study was undertaken to determine performance of intraperitoneal osmotic pumps in finishing cattle concurrently being administered estrogen. Six hundred seventy-two cross-bred large frame cattle weighing approximately 412 kg were bought and assigned to a control group and six treatment groups of 96 cattle each. The cattle were implanted with intraperitoneal osmotic pumps capable of delivering 6, 12, 15 or 18 mg bST per day during an 84-day period ending with slaughter. The cattle received subcutaneous estrogen pellets during a 1 26-day period ending with slaughter. The estrogen release is estimated at about 200 ug/d. The results are shown in the following table:

TABLE

| | | TREATMENT | | | | |
|---|---|---|---|---|---|---|
| | | 30% bST Load | | 40% bST Load | 45% bST Load | |
| Parameters | Control | 6 mg/d | 12 mg/d | 15 mg/d 6 mg/d | 12 mg/d | 18 mg/d |
| Initial Body Wt (kg) | 411.9 | 411.9 | 411.9 | 411.9 411.9 | 411.9 | 411.9 |
| Final Body Wt (kg) | 555.1$^a$ | 565.6$^{bc}$ | 568.7$^{bc}$ | 569.6$^c$ 561.8$^b$ | 563.5$^{bc}$ | 566.5$^{bc}$ |
| Carcass Wt (kg) | 343.0$^a$ | 353.1$^{bc}$ | 355.4$^{cd}$ | 357.2$^d$ 350.8$^b$ | 351.3$^b$ | 353.8$^{bcd}$ |
| Dressing Percent (%) | 61.8$^a$ | 62.4$^b$ | 62.8$^b$ | 62.4$^b$ 62.4$^b$ | 62.4$^b$ | 62.5$^b$ |
| Carcass Response (%) | — | 96% | 104% | 86% 116% | 99% | 95% |
| Non-Carcass Response (%) | — | 4% | –9% | 14% –16% | 1% | 5% |

$^{a,b}$different superscripts indicate that numbers in a row are significantly different (p <.05).

The results of Examples B3 and B4 indicate that concurrent intraperitoneal treatment of finishing beef cattle with intraperitoneal bST and estradiol significantly increase dressing percentage and carcass weight and furthermore allocate most of the increased weight to the carcass components.

What is claimed:

1. A method of implanting large diameter objects in the intraperitoneal cavity of bovines which can be accomplished readily, without significant injury to the bovine, requires minimal care after implantation, and rapidly heals, comprising:

providing a generally cylindrical large diameter object having an outside diameter in the range of about 8 to about 15 millimeters (mm);

making an incision of less than about 25 mm in length in the hide of the left paralumbar fossa of a bovine, the incision effective for passing a first portion of a generally cylindrical tube which itself functions as a trocar therethrough which has a external diameter of less than about 25 mm and which has an internal diameter for passing the large diameter object therethrough, the incision having an orientation and length and depth such that gaping of the resulting wound substantially does not occur after inserting the tube and the object therethrough and removing the tube therefrom;

inserting into the incision said generally cylindrical tube, said generally cylindrical tube further having a non-hide-incising tip effective for penetrating tissues underlying the incision, and for puncturing the peritoneum, and having a length for extending through the incision, underlying tissues, and into the intraperitoneal cavity of the bovine;

causing the tip of the tube to penetrate the underlying tissues and to puncture the peritoneum and inserting the large diameter object therethrough into the intraperitoneal cavity of the bovine; and removing the tube.

2. The method of claim 1 wherein:
the incision comprises a vertical incision.

3. The method of claim 1 wherein:
the inserting step is conducted at a time when the rumen is not distended significantly into a portion of the peritoneal cavity being targeted.

4. The method of claim 1 wherein:
the bovine is a bovine fasting or feed-restricted for 6 to 24 hours prior to implantation.

5. The method of claim 1 wherein:
the bovine is a bovine fasting or feed-restricted for 10 to 18 hours prior to implantation.

6. The method of claim 1 wherein:
the opening of the hide is less than about 20 mm.

7. The method of claim 1 wherein:
the object is an osmotic pump capable of delivering about 3 to about 14 mg/day of bovine somatotropin for a period of greater than 9 weeks and optionally containing an estrogenic agent.

8. The method of claim 1 wherein:
the tube and its contents are sterilely packaged with the large diameter objects therein and sterility is maintained until immediately prior to the inserting step.

9. The method of claim 1 wherein:
the sterility of an outside portion of the tube which will extend from hide to peritoneal cavity is maintained by a sheath removable prior to use.

10. The method of claim 1 wherein:
the incision is substantially through the hide only.

* * * * *